US007335153B2

(12) United States Patent
Seul et al.

(10) Patent No.: US 7,335,153 B2
(45) Date of Patent: Feb. 26, 2008

(54) ARRAYS OF MICROPARTICLES AND METHODS OF PREPARATION THEREOF

(75) Inventors: Michael Seul, Fanwood, NJ (US); Chiu Wo Chau, Edison, NJ (US); Hui Huang, Piscataway, NJ (US); Sukanta Banerjee, North Brunswick, NJ (US); Jiacheng Yang, Hillsboro, NJ (US); Ye Hong, Piscataway, NJ (US)

(73) Assignee: Bio Array Solutions Ltd., Warren, NJ (US)

( * ) Notice: Subject to any disclaimer, the term of this patent is extended or adjusted under 35 U.S.C. 154(b) by 580 days.

(21) Appl. No.: 10/192,352

(22) Filed: Jul. 9, 2002

(65) Prior Publication Data

US 2003/0082587 A1    May 1, 2003

Related U.S. Application Data

(60) Provisional application No. 60/343,621, filed on Dec. 28, 2001.

(51) Int. Cl.
*C40B 20/02* (2006.01)
(52) U.S. Cl. .................................. 506/3; 435/6
(58) Field of Classification Search ................ 436/518, 436/524, 528, 531, 164, 172; 435/4, 174, 435/180
See application file for complete search history.

(56) References Cited

U.S. PATENT DOCUMENTS

| | | | |
|---|---|---|---|
| 3,790,492 A | 2/1974 | Fulwyler | |
| 4,267,235 A | 5/1981 | Rembaum et al. | |
| 4,326,008 A | 4/1982 | Rembaum | |
| 4,487,855 A | 12/1984 | Shih et al. | |
| 4,613,559 A | 9/1986 | Ober et al. | |
| 4,774,189 A | 9/1988 | Schwartz | |
| 5,073,498 A | 12/1991 | Schwartz et al. | |
| 5,194,300 A | 3/1993 | Cheung | |
| 5,266,467 A | 11/1993 | Imai et al. | |
| 5,298,741 A | 3/1994 | Walt et al. | |
| 5,326,692 A | 7/1994 | Brinkley et al. | |
| 5,415,835 A | 5/1995 | Brueck et al. | |
| 5,516,635 A | 5/1996 | Ekins et al. | |
| 5,532,128 A | 7/1996 | Eggers et al. | |
| 5,593,839 A | 1/1997 | Hubbell et al. | |
| 5,723,218 A | 3/1998 | Haugland et al. | |
| 5,770,358 A | 6/1998 | Dower | |
| 5,786,219 A | 7/1998 | Zhang et al. | |
| 5,812,272 A * | 9/1998 | King et al. .................. | 356/445 |
| 5,900,481 A | 5/1999 | Lough et al. | |
| 5,922,617 A * | 7/1999 | Wang et al. ................. | 436/518 |
| 5,948,621 A * | 9/1999 | Turner et al. ................... | 435/6 |
| 5,959,098 A * | 9/1999 | Goldberg et al. .......... | 536/25.3 |
| 5,961,923 A | 10/1999 | Nova et al. | |
| 5,988,432 A | 11/1999 | Sun | |
| 6,023,540 A | 2/2000 | Walt et al. | |
| 6,083,763 A | 7/2000 | Balch | |
| 6,096,368 A | 8/2000 | Sun | |
| 6,133,436 A | 10/2000 | Koster et al. | |
| 6,153,375 A * | 11/2000 | Kobylecki et al. ............. | 435/4 |
| 6,172,218 B1 | 1/2001 | Brenner | |
| 6,209,589 B1 | 4/2001 | Hare et al. | |
| 6,251,691 B1 | 6/2001 | Seul | |
| 6,266,459 B1 | 7/2001 | Walt et al. | |
| 6,268,222 B1 | 7/2001 | Chandler et al. | |
| 6,327,410 B1 | 12/2001 | Walt et al. | |
| 6,355,491 B1 | 3/2002 | Zhou et al. | |
| 6,429,027 B1 | 8/2002 | Chee et al. | |
| 6,713,309 B1 * | 3/2004 | Anderson et al. ........... | 436/518 |

FOREIGN PATENT DOCUMENTS

| | | |
|---|---|---|
| CA | 1248873 | 1/1989 |
| WO | WO 93/06121 | 4/1993 |
| WO | WO 93/24517 | * 12/1993 |
| WO | WO 97/40385 | 10/1997 |
| WO | WO 98/40726 | 9/1998 |
| WO | WO 98/53300 | 11/1998 |
| WO | WO 99/18434 | 4/1999 |
| WO | WO 99/19515 | 4/1999 |
| WO | WO 99/60170 | 11/1999 |
| WO | WO 00/04372 | 1/2000 |
| WO | WO 00/13004 | 3/2000 |
| WO | WO 00/75373 | 12/2000 |

OTHER PUBLICATIONS

P-A Clerc et al., "Advanced deep reactive ion etching: a versatile tool for microelectromechanical systems", Dec. 1998, J. Micromech. Microeng., vol. 8, No. 4, pp. 272-278.*
Glossary of Terms Used in Physical Organic Chemistry, IUPAC Recommendations 1994, T to Z, http://www.chem.qmul.ac.uk/iupac/gtpoc/TtZ.html.*
Lander, Eric S. "Array of Hope". *Nature genetics Supplement, Perspective.* Jan. 1999, 3-4, vol. 21.
Battersby, Bronwyn J, et al. "Toward Larger Chemical Libraries: Encoding with Fluorescent Colloids in Combinatorial Chemistry." *J. Am. Chem. Soc.* Feb. 17, 2000, 2138-2139.
Grondahl, Lisbeth, et al. "Encoding Combinatorial Libraries: A Novel Application of Fluorescent Silica Colloids." *Langmuir.* Nov. 10, 2000, 9709-9715.
International PCT Search Report.
Goodey, et al., "Development of Multianalyte Sensor Arrays Composed of Chemically Derivatized Polymeric Microspheres Localized in Micromachined Cavities," Journal of the American Chemical Society, vol. 123: 2559-2570 (2001).

* cited by examiner

*Primary Examiner*—J. Douglas Schultz
*Assistant Examiner*—Jeffrey S. Lundgren
(74) *Attorney, Agent, or Firm*—Eric P. Mirabel

(57) ABSTRACT

This invention provides high unit density arrays of microparticles and methods of assembling such arrays. The microparticles in the arrays may be functionalized with chemical or biological entities specific to a given target analyte. The high unit density arrays of this invention are formed on chips which may be combined to form multichip arrays according to the methods described herein. The chips and/or multichip arrays of this invention are useful for chemical and biological assays.

12 Claims, 22 Drawing Sheets

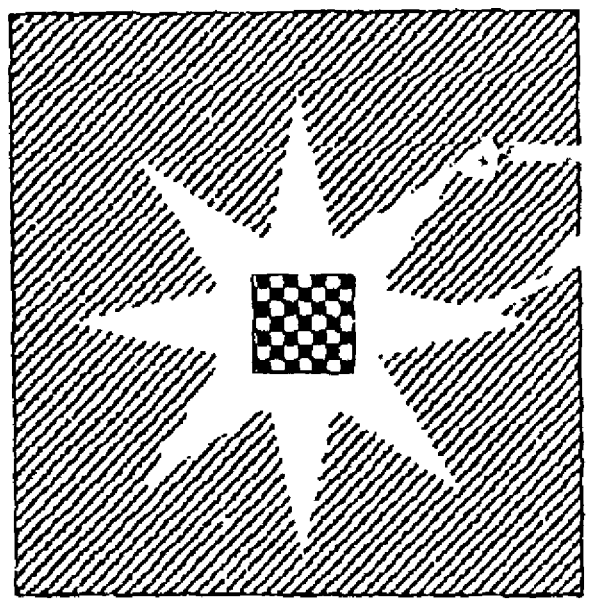
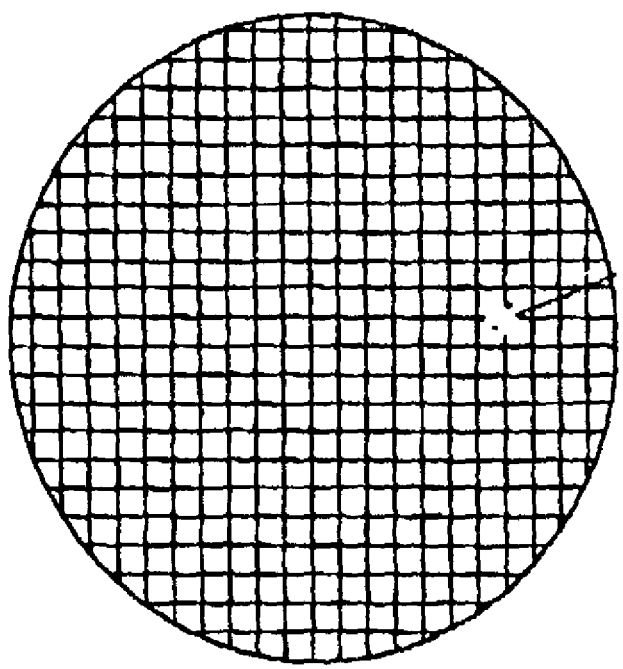
Fig. 3

1. Surface pattern
2. The array is composed of 4012 hexagonal sites with detailed dimensions as follows:
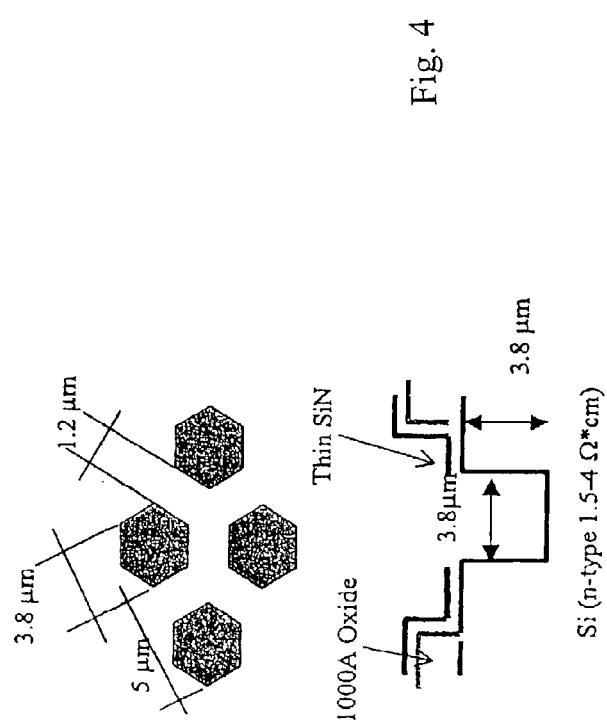
Fig. 4

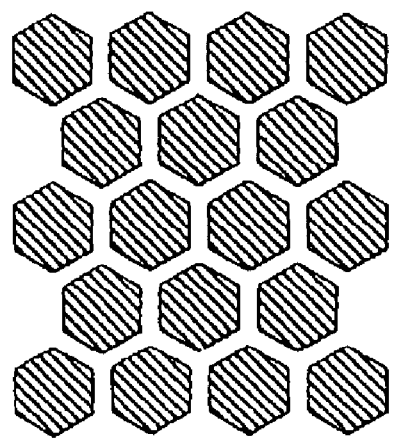
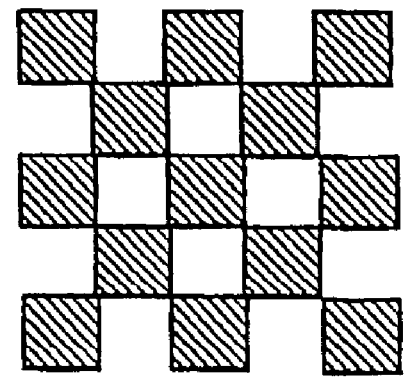
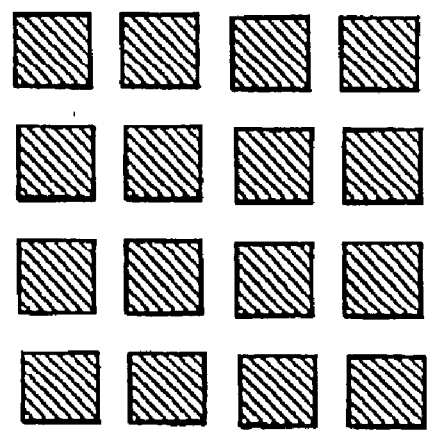
Fig. 6 a) Gel formed on wafer
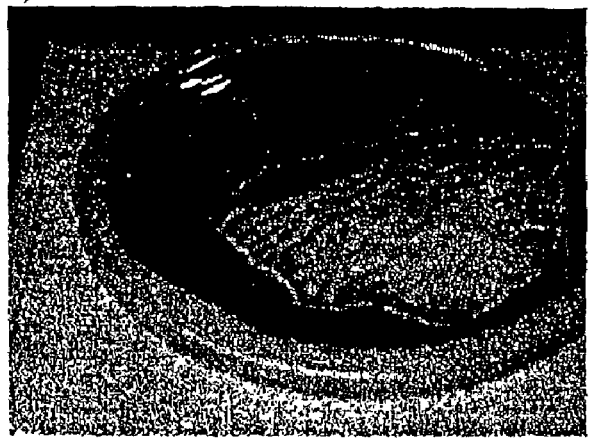
b) Gel peeled from wafer
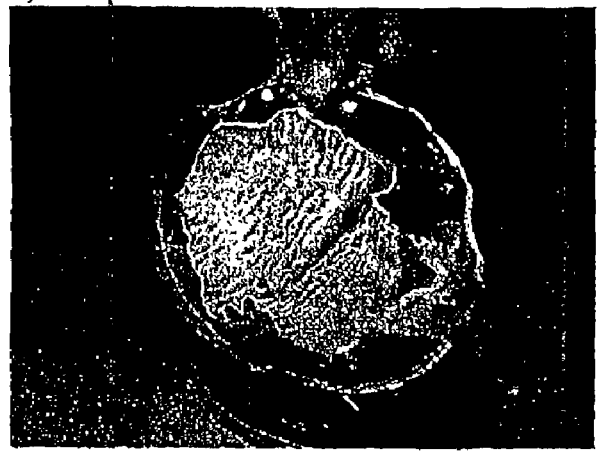
c) Cleaned wafer
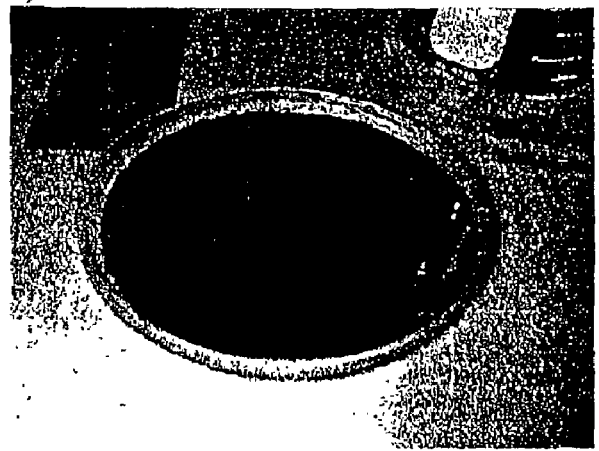
Fig. 12

Image of beads on a chip before gel formation
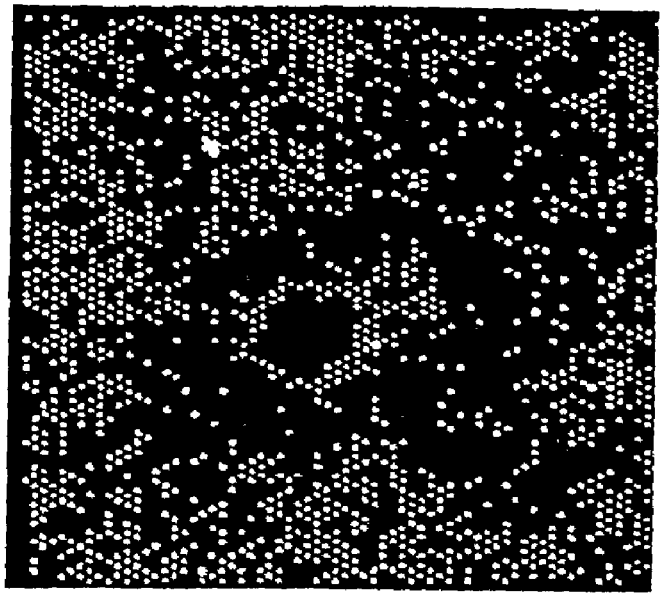
Image of beads on the chip after gel is peeled off
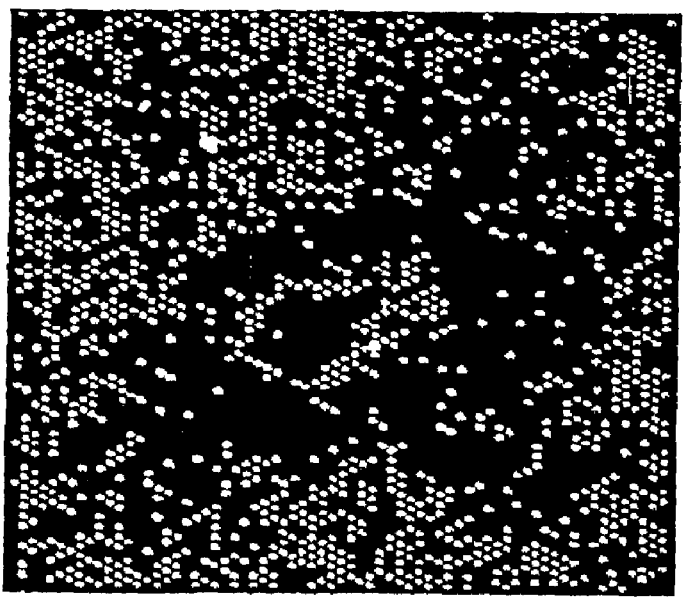
Fig. 13(a)

(1) Assay signal on chip without treatment of hydrogel
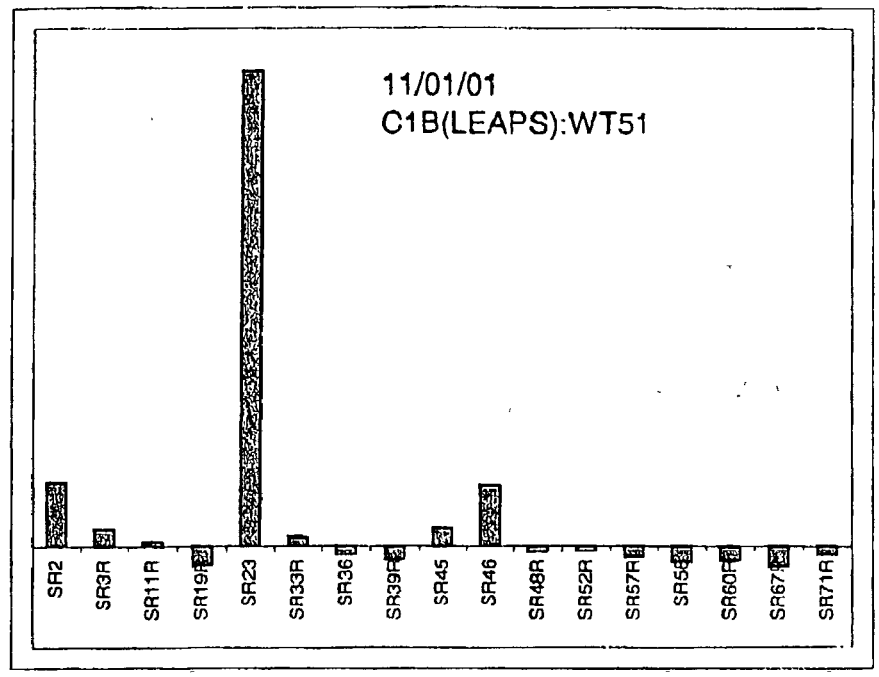
(2) Assay signal on chip with treatment of hydrogel
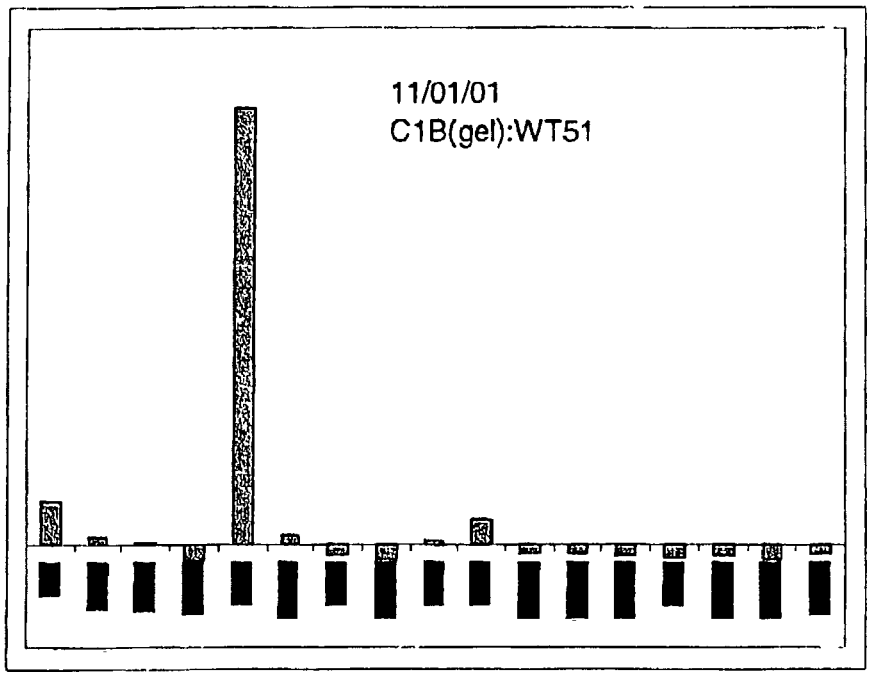
Fig. 13(b)

2 types of recesses (1 and 2, differ in size or shape) in the same array

ARRAYS OF MICROPARTICLES AND METHODS OF PREPARATION THEREOF

This application claims priority to U.S. Provisional Application 60/343,621 filed on Dec. 28, 2001. U.S. Provisional Application 60/343,621 is hereby incorporated by reference in its entirety.

FIELD OF THE INVENTION

This invention relates to high unit density arrays of microparticles and methods of making same. This invention also relates to multichip arrays and their methods of manufacture. This invention further provides methods for performing bioassays using high unit density arrays and multichip arrays.

BACKGROUND OF THE INVENTION

An array format for biological and chemical analysis holds the promise to rapidly provide accurate results while minimizing labor. [Nature Genetics, 1999 Vol. 21 (1) supplement pp.3-4] Typically, arrays of biological probes such as DNA, RNA or protein molecules are formed either by deposition and immobilization or by in-situ synthesis on inert substrates. In these prior art methods, array formation is usually accomplished by attaching probe molecules directly to a substrate, which may be composed of organic materials (such as polymeric materials like nitrocellulose) or inorganic materials (such as glass or silicon).

The use of silicon as a substrate provides certain advantages related to the well-established methods of semiconductor wafer and chip processing. In semiconductor processing, wafers are modified and transformed in a series of multiple processing steps to create desirable features. Usually, a plurality of identical features are made on each wafer simultaneously by parallel processing to form individual segments on a wafer. Dramatic savings in manufacturing time are achieved by fabricating identical features using parallel or batch processing. In addition, batch processing yields high chip uniformity, and by using certain photolithography and etching methods, very small (sub-micron) features can be precisely fabricated. Accordingly, structures with high feature densities can be fabricated on a very small chip. After processing is completed, the individual segments are cut from wafers in a process known as singulation, to obtain a multiplicity of chips. [Peter Van Zant, "Microchip Fabrication", 3$^{rd}$ edition, McGraw-Hill 1998].

Semiconductor wafers containing different functional chips can be combined either in final packaging processes by interconnecting different chips or simply by bonding two wafers with different functional chips, then cleaving the stack of wafers. The high efficiency of the semiconductor fabrication process has significantly contributed to the rapid growth of the industry. Highly sophisticated systems have been developed for chip production, packaging, and quality control.

Biochips are arrays of different biomolecules ("probes") capable of binding to specific targets which are bound to a solid support. There have been essentially two methods to prepare biochips.

The first method involves placing aliquots of solutions containing pre-synthesized probe molecules of interest on a planar substrate, followed by immobilizing the probe molecules in designated positions. For example, probe solutions can be dispensed ("spotted") on a substrate to form a positionally encoded one-dimensional [Kricka, Larry J., "Immunoassay", Chapter 18, pages 389-404, Academic Press, 1996] or two-dimensional [U.S. Pat. Nos. 5,807,755 and 5,837,551] probe arrays of customized composition. Molecular probes may be directly attached to a substrate surface or may be attached to solid phase carriers, which in turn are deposited on, or attached to a substrate to form an array. Microparticles ("beads") represent one type of such carrier. Beads offer the advantage of separating the process of preparing and testing substrates from the process of preparing, applying and testing probe and assay chemistries [U.S. Pat. No. 6,251,691]. Beads of various sizes and compositions have been extensively used in chemical and biochemical analysis as well as in combinatorial synthesis.

The deposition, printing and spotting methods for probe array production have several undesirable characteristics. First, even state-of-the-art deposition and printing technologies only produce arrays of low feature density, reflecting typical spot dimensions of 100 microns and spot-to-spot separations of 300 microns. Second, methods of probe deposition described to date have failed to produce uniform spots, with significant spot-to-spot variations. Third, spotting methods, including such variants as electrophoretic deposition to patterned electrodes [U.S. Pat. No. 5,605,662], require substantial instrumental and logistical support to implement the production of arrays on any significant scale. In particular, spotting methods do not support batch fabrication of probe arrays. That is, while a batch processing format may be used to produce substrates efficiently, the subsequent step of "bio-functionalizing" these substrates by applying chemical or biochemical probes is inefficient, because it does not conform to a batch format but instead requires many individual spotting steps. Thus, this process of manufacturing large numbers of identical functionalized chips is far more time-consuming and expensive than a process that uses parallel processing procedures.

The second method of preparing probe arrays involves in-situ photochemical synthesis of linear probe molecules such as oligonucleotides and peptides using a process similar to photolithography, a standard component of semiconductor processing. These methods have been most widely used in recent years to synthesize, in a parallel set of multi-step photochemical reactions, sets of oligonucleotides in designated sections of glass or similar substrates [U.S. Pat. No. 5,143,854; Proc. Nat. Acad. Sci. USA, 1996, 93: 13555-13560].

Although parallel processing to generate simultaneously a multitude of probe arrays directly on a wafer has the advantage of the scalability and intrinsic improvement in uniformity afforded by batch processing, serious drawbacks exist for the fabrication of probe arrays. First, only simple, relatively short linear molecules are suitably synthesized in a series of single step reactions, and in practice, only arrays of short oligonucleotides have been prepared by this method. Second, the reactions often do not proceed to completion, leading to significant compositional heterogeneity. Third, all semiconductor processing must be completed prior to the introduction of biomolecules, because biomolecules may not be compatible with the harsh environments in certain semiconductor processing steps. This limitation can preclude one from taking full advantage of the wide variety of semiconductor fabrication techniques. Fourth, if functionalization is performed in a batch fabrication format, that fabrication process defines the chemical or biochemical composition ("content") of each chip on the wafer. That is, to introduce a change in probe design requires that the entire fabrication process be changed accordingly. Customization, while theoretically feasible, requires a change in the sequence of requisite masking steps required for photochemical synthesis of a desired set of probe molecules. The cost and time delays associated with this process renders customization infeasible in practice.

BRIEF DESCRIPTION OF THE DRAWINGS

FIG. 3 shows an example of wafer design.

FIG. 4 shows an example of the design of chips comprising bead arrays. The substrate is silicon (Si). The 12-tip star pattern is on a 100 nm thick layer of $SiO_2$. The area inside the star has no $SiO_2$ covering while the area outside the star has an $SiO_2$ covering. In the center, there is an array of closely packed hexagonal recesses. The total number of the recesses is 4012.

FIG. 6 shows examples of array structures. A1 and A2 are arrays of rectangular recesses. A3 is an array of hexagonal recesses.

FIG. 12 is a photograph of hydrogel formed on silicon wafer.

FIG. 13a is an illustration of the fluorescent images of a bead array on a chip before hydrogel formation and after gel peeling. The number of beads and bead positions were identical. FIG. 13b is an illustration of on-chip reaction results with hydrogel treatment and without hydrogel treatment.

SUMMARY OF THE INVENTION

Figure 1A:
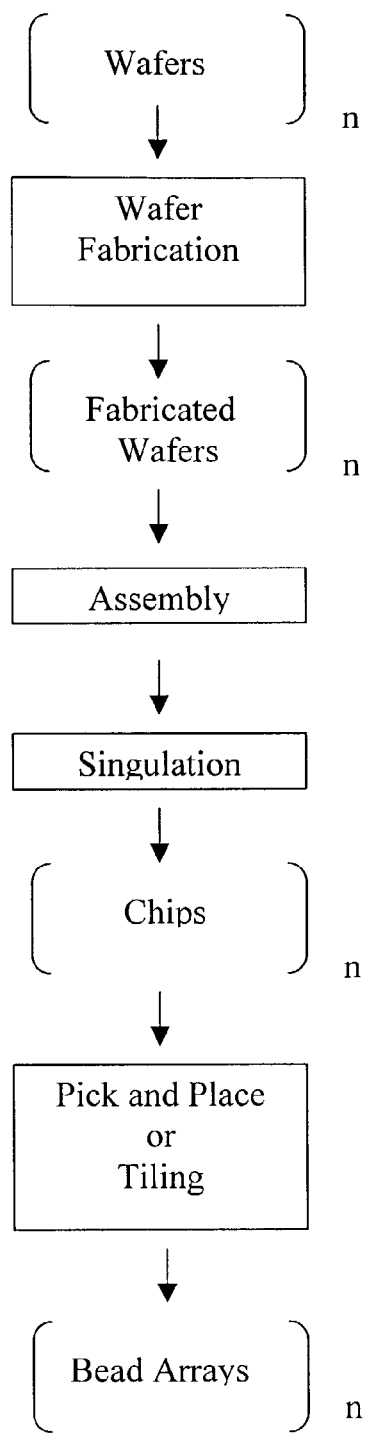
FIGS. 1a and 1b are an illustration of the process of the invention.

The present invention provides a parallel processing method that takes advantage of semiconductor fabrication methods. In addition, the methods in this invention are flexible enough to address different quantity and different assay requirements. The invention combines the flexibility of being able to select the array content with the high feature density and economies of scale afforded by parallel (batch) array assembly. This invention provides a process for the assembly of random encoded, solid carrier-displayed probe arrays of selectable composition in designated positions within delineated compartments on a substrate which may then be fractionated into a plurality of chips having arrays of carrier-displayed probes. In another embodiment, singulated chips (without solid carrier-displayed probes) derived from one or more substrates are contacted with a desired population of solid carrier-displayed probes to form chips having the desired array. The formation of multichip arrays is also provided by combining chips prepared from different substrates having different populations of carrier-displayed probes. The invention also describes designs of substrates and chips displaying solid phase carriers such as chemically tagged microparticles so as to optimize the performance of chip-displayed microparticle arrays in bioanalytical tests and assays for various target analytes including biomolecules such as nucleic acids, proteins, cells and the like.

The method for producing biochips according to this invention comprises patterning a substrate to form a plurality of chip regions, delineating a separating boundary between the chip regions, assembling at least one bead array comprising bio-functionalized, optically encoded beads on a surface of the substrate, and singulating the chip regions to form individual biochips. As discussed above, singulation may be accomplished prior to assembling a bead array on a chip surface. (In this context, the term "biochip," as used herein refers to a chip having biomolecules attached to its surface, e.g., for use in bioanalysis.) Non-limiting examples of biomolecules include oligonucleotides, nucleic acid fragments, proteins, oligopeptides, ligands, receptors, antigens, antibodies, and individual members of biological binding pairs. Further, the term "singulate" or "singulation" as used herein refers to a process to obtain chips by breaking the connections between individual chip regions on a substrate or a subunit of a substrate containing more than one chips. Also, the terms "functionalization" and "biofunctionalization" as used herein refer to a process to bind biomolecules (e.g., molecular probes) to a substrate, including attaching to bead surfaces.)

This invention also provides a method of making an assay device comprising a plurality of molecular probes. The method comprises choosing a molecular probe from a probe library and affixing it to a plurality of beads to form a bead sub-population. The bead sub-population is affixed to a major surface of a substrate comprised of chips possessing a decodable tag that identifies the wafer of origin. The wafer is then singulated to produce a plurality of biochips. The process is repeated with at least one other bead sub-population comprising a different molecular probe. The resulting biochips are then assembled to form a bioarray.

Another aspect of this invention are the assay devices prepared according to the method described above.

The devices of this invention include substrates that have been partitioned to define separable chip regions. Such substrates optionally may comprise further patterning and partitioning to define subregions for restraining one or more solid carriers, e.g. beads.

In another embodiment, this invention comprises the partitioned and optionally patterned substrates which further comprise one or more populations of solid carrier probes for detecting a target analyte.

The singulated chips formed by the fractionation of wafers described above, with or without the solid carrier-probe arrays is also an embodiment of this invention. Preferably, the chips comprise a solid carrier-probe array.

This invention also includes assay devices for detecting one or more target analytes. Such assay devices of this invention comprise one or more biochips comprising an array of functionalized beads suitable for detecting one or more desired target analytes. In a preferred embodiment, a plurality of different biochips are affixed to a carrier to provide the ability to detect different target analytes.

Another aspect of this invention is to provide a method for performing bio-assays comprising contacting a plurality of biochips bonded to a carrier with a solution comprising at least one target analyte, and detecting the analyte directly or indirectly. The plurality of biochips may comprise at least one sub-populations of biochips with a bio-functionalized array. Optionally, the plurality of biochips may comprise at least two sub-populations of biochips wherein the biochips of the different sub-populations are different sizes or different bead array geometries.

Yet another aspect of this invention is to provide a method of performing an assay using the assay devices described above. The method comprises exposing a biochip array of the assay device to a solution containing at least one target analyte and detecting the reaction products.

Another aspect of this invention is to provide a method for fabricating a carrier for biochips comprising covering a solid substrate that has at least one hydrophilic major surface with a patterned hydrophobic layer that is used to spatially define an array of biochips.

This invention also provides a process of assembling bead arrays on a surface of a semiconductor substrate comprising placing a patterned dielectric film on a surface of the semiconductor substrate, wherein the dielectric film forms boundaries on the substrate surface, and adding beads in a solution to a region of the substrate designated for bead arrays, wherein the region is defined by the boundaries.

Another aspect of this invention is to provide a process for directly depositing beads on a surface of a semiconductor substrate to form a bead array, said process comprising adding a solution of beads to the surface of a patterned semiconductor substrate containing structures for housing the beads and mechanically agitating the solution to induce the beads to settle in the structures.

Yet another aspect of this invention is to provide a bead array comprising a removable coating for protecting the bead array on a biochip. In this aspect, the bead array comprises a plurality of beads with surfaces to which molecular probes are attached, and the coating has the property of being non-reactive towards the molecular probes on the surfaces of the beads.

This invention also provides a method for quality control during the fabrication of a biochip. This method comprises optically encoding bio-functionalized beads, exposing a patterned substrate containing recesses for housing beads to a solution containing the beads, and optically imaging the beads to ensure that the recesses are substantially occupied.

DETAILED DESCRIPTION OF THE INVENTION

This invention provides compositions and methods to design and produce arrays of desired composition and layout comprising chemical or biological entities, such as biomolecules like nucleic acids and proteins. Specifically, the methods of the invention described herein combine the flexibility of real-time selection of array content and high feature density with the economies of scale afforded by a parallel process for the assembly of a multiplicity of random encoded, solid carrier-displayed probe arrays of selectable composition, in designated positions of delineated wafer compartments ("chips"). The invention also includes methods for the formation of positionally and compositionally encoded arrays of such chips. Further, the invention provides wafer and chip designs that optimize performance of solid phase carriers such as tagged microparticles ("beads") and tagged chips ("tiles") in bioanalytical tests and assays involving biomolecules and cells.

This invention provides methods and processes for making high unit density arrays of microparticles which are biologically or chemically functionalized. Such arrays can be produced in adjustable quantities, in a flexible format and with pre-selected compositions. The methods and processes of the invention can be conducted in a batch and parallel format. Specifically, the invention relates to the fabrication of such arrays of microparticles on one or more wafers, such that a part or the entirety of a specific wafer displays one or more such microparticle arrays with a composition and functionality which can be pre-selected. The invention also relates to the packaging of the resulting array of microparticles in a multichip format.

The present invention provides arrays with compositions that depend on the end use of the array. Arrays containing from about one bead to many millions can be made. Generally the array will comprise from one to as many as a billion or more, depending on the size of the beads and the substrate, as well as the end use of the array. Preferred ranges for high feature density array are from about 1,000,000,000 (1 billion) to 1 beads/mm$^2$, more preferably 1,000,000 to 100 beads/mm$^2$, most preferably 100,000 to 1,000 beads/mm$^2$.

The microparticles of the invention are functionalized to include chemical or biological entities such as, for example, DNA, RNA and proteins. These entities can be selected depending on the application of interest thereby providing flexibility of selection of array content. In addition, since such an array of microparticles has a high feature density, it can be designed to optimize the array performance in the bioanalytical assay of interest. Examples of such assays are disclosed in PCT/US01/20179 and U.S. Pat. No. 6,251,691 which are all incorporated herein by reference.

Figure 1B:
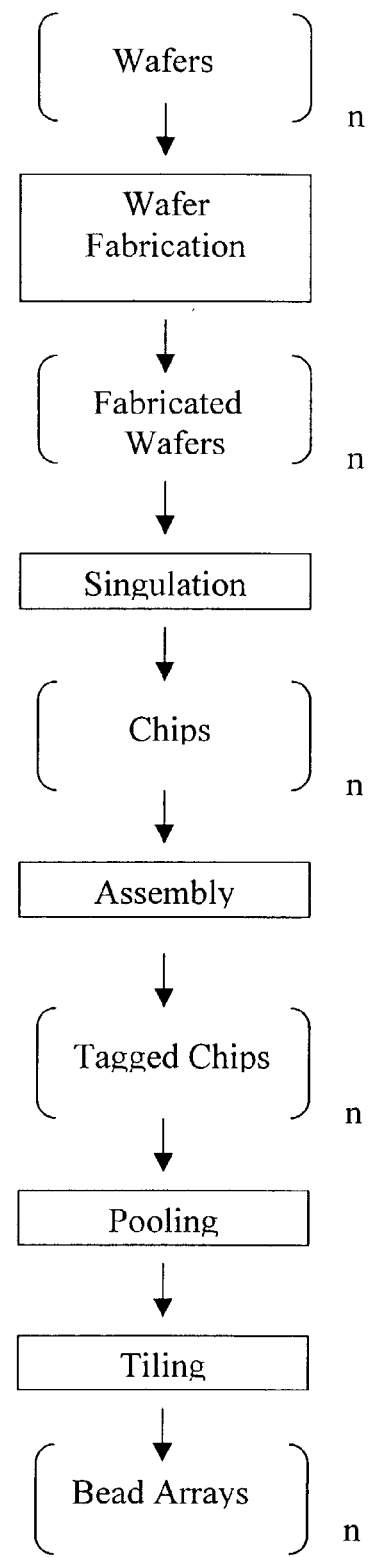

The methods of the overall process of the present invention can be grouped into four general categories, namely pre-assembly, assembly, post-assembly and packaging. Such grouping is not intended to limit certain methods to certain groups. FIGS. 1a and 1b are particular illustrations of the process of the invention as further described below.

I. Pre-Assembly

The methods of pre-assembly include the implementation of chip layout, fabrication of the wafer based on such layout, optionally scribing of the wafer, followed by cleaning and inspection, if required. As illustrated in FIGS. 1a and 1b, singulation (as described below) may follow the methods of assembly (FIG. 1a) or follow the method of wafer fabrication (FIG. 1b). In the event that individual chips are obtained from a wafer, the resulting chips are grouped and each chip may be labeled as described below to identify such chip based on its functionalization history.

1.1 Chip Layout

Figure 2:
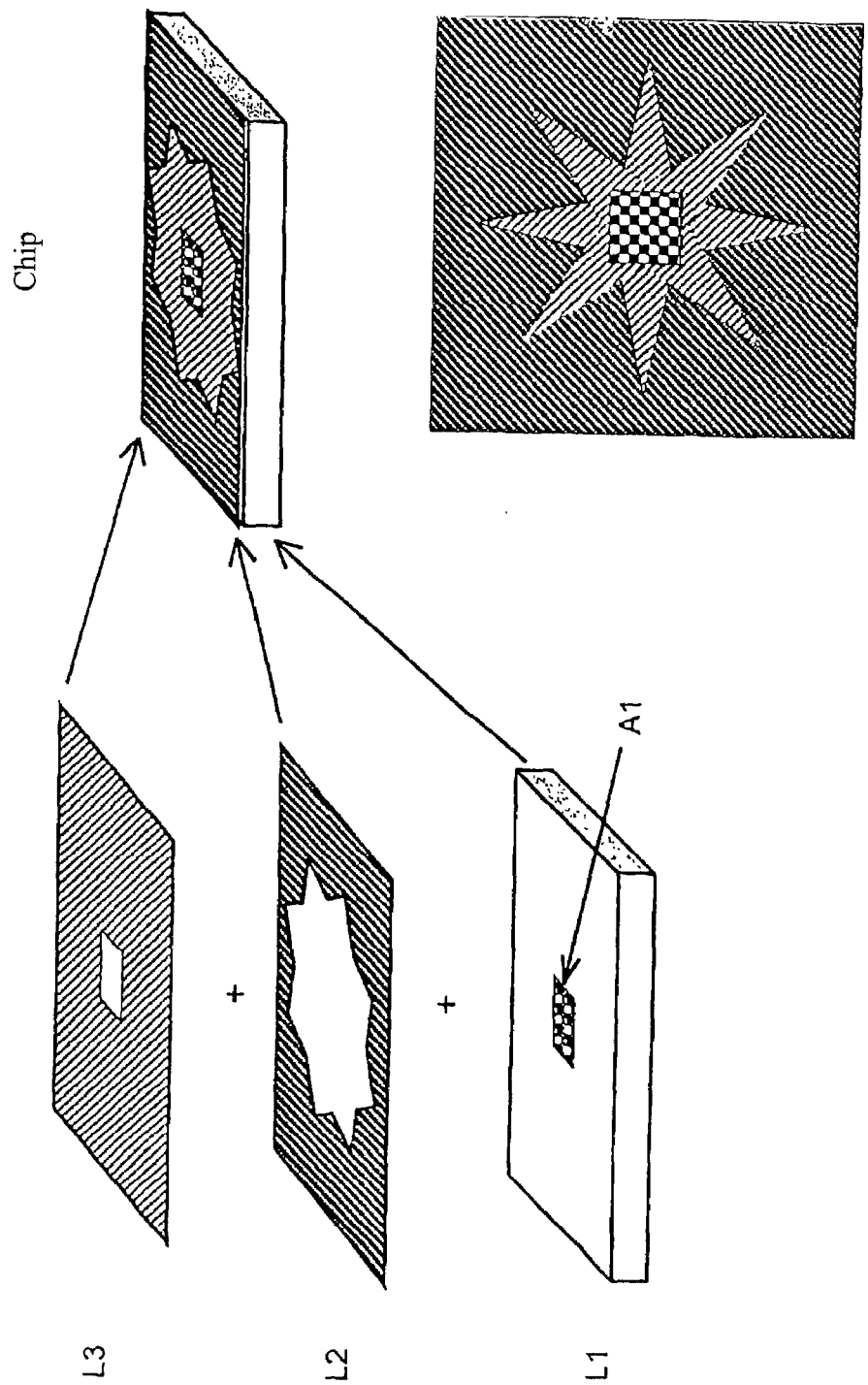
FIG. 2 shows an example of a chip comprising a bead array. The chip is comprised of three layers (L1, L2, L3). L1 is a silicon substrate with a micromachined array to accommodate beads (A1); L2, patterned $SiO_2$ (100 nm thick); L3, is a layer of $Si_3N_4$ (5-10 nm thick).

An example of chip layout is shown in FIG. 2. It is to be understood that a "chip" may be any three-dimensional shape. Each chip comprises a substrate (e.g., layer 1 (L1)) where bio-functionalized beads can be assembled to form an array of microparticles. Many types of materials may be used as a substrate. Suitable materials have certain desirable characteristics. These characteristics can be classified as mechanical (e.g., strength), electrical (e.g., having an interfacial impedance that can be modified), optical (e.g., flatness, transparency, a well-defined optical absorption spectrum, minimal auto-fluorescence, high reflectivity) and chemical (e.g., amenable to processes for defining precise features or for depositing dielectric layers, surface reactivity that permits covalent linkages). Non-limiting examples of suitable substrates include semiconductors (e.g., silicon), insulators (e.g., sapphire, mica, and ruby), ceramic materials, and polymers (e.g., Mylar™, Kapton™, and Lucite™).

In certain embodiments, the substrate can be a semiconductor wafer, such as single crystal semiconductor wafers which are commonly used in the semiconductor device industry. In other embodiments, the substrate can be any patternable solid substrate selected to be inert to the reagents used in chip fabrication and bioassays. Non-limiting examples of such substrates include glass, plastics, and polymers.

FIG. 2 is an illustration of a chip having a rectangular cross-section and is not intended to limit other chip geometries. In FIG. 2, L1 is represented as a middle layer (although the layers on both sides of L1 are not required). The recess array A1 of L1 is where the bead array is to be built. The shape of the recesses A1 need not be square. Non-limiting examples of other suitable shapes include triangles, rectangles, pentagons, hexagons, and circles. One of the functions of recess array A1 is to help arrange and secure the beads by building regular structures on the wafer or chips to confine the movement of beads on the surface.

Optionally, the chip may also contain a second layer (L2). Layer L2 comprises a patterned insulating dielectric layer (for example, silicon dioxide). One example of a possible pattern is given by FIG. 3, which shows a star-shaped pattern in the middle of the chip. The heavily shaded area is the dielectric material and the white area is where the dielectric is removed. The thickness of the dielectric layer is typically, but is not limited to, 100 nm. If an electric field is applied vertically through the chip, a non-uniform potential near the surface of the chip due to the L2 pattern is formed. The electric field may be applied to the surface in accordance with the process set forth in U.S. Pat. No. 6,251,691 incorporated herein by reference (such a process is referred to as "LEAPS"). Using LEAPS, beads in a liquid solution that is applied to the surface of the substrate are subjected to a change in the lateral electric field gradient when an AC potential is applied to the substrate. This electric field gradient drives the beads in the solution so that the beads will accumulate in area A1 where surface structures have been built on L1. Accordingly, the pattern of L2 can be any pattern that may cause bead accumulation in a particular area of the substrate, although it should be recognized that some patterns are more efficient at causing beads to accumulate than others.

Patterning of the dielectric layer L2 in accordance with a pre-determined design facilitates the quasi-permanent modification of the electrical impedance of the electrolyte-insulator-semiconductor (EIS) structure formed by the bead solution-dielectric-semiconductor. By spatially modulating the EIS impedance, electrode-patterning determines the ionic current in the vicinity of the electrode. Depending on the frequency of the applied electric field, beads either seek out, or avoid, regions of high ionic current. Spatial patterning therefore conveys explicit external control over the placement and shape of bead arrays.

Optionally, a chip comprising a bead array may contain a protective passivation layer, usually covering the surface. Layer L3 functions as an interface between the chip and liquid media, which can include the bead suspension, bioassay samples, or chip washing chemicals. Accordingly, layer L3 should be relatively robust against corrosion from chemicals and the ambient environment. It also should protect the functional probes attached to the beads from electrostatic damage during bead array assembly. In some embodiments, layer L3 also minimizes the adhesion of beads to the chip surface during bead array assembly. Layer L3 is preferably inert to biological samples and is preferably non-fluorescent in the same wavelength range as that used for fluorescent detection in bioassays. In addition, its existence should not create a change in the electric field distribution near the chip surface which would prevent the use of LEAPS for bead assembling. By way of example, the layer L3 may be a thin layer of LPCVD (low pressure chemical vapor deposited) silicon nitride with a thickness of from about 40 to about 100 Å.

Layer L3 can also be engineered by chemical treatments to alter the surface properties. For example, a silicon nitride surface could be oxidized to yield $SiO_x$ (i.e., $SiO_2$ and/or substoichiometric silicon oxide) or silicon oxynitride ($SiO_xN_y$), both of which are hydrophilic and would facilitate dispensing aqueous samples. In other embodiments, the surface $SiO_x$ or $SiO_xN_y$ can be further functionalized with silanol groups to yield a hydrophobic surface.

Finally, the backside of each chip can be coated with a metal or metal alloy for electric contact (preferably an ohmic contact). For example, if the chip is made from a silicon substrate, the backside of the chip can be coated with a thin chromium adhesion layer and a thicker gold layer, using routine processes in the semiconductor industry. Although the gold coating is useful because it is inert to most chemicals and has high conductivity, other ohmic contact coatings can be used if they are chemically compatible with the other fabrication processes. Non-limiting examples include titanium nitride/tungsten and titanium tungsten/tungsten. The chips may be coated with a metal or metal alloy before or after singulation.

Optionally, one side of a chip and/or its parallel opposite side can be coated with a magnetically responsive material. This can be achieved by assembling magnetic beads on either or both sides of the chip magnetic beads using routine assembly methods. The methods set forth in U.S. Ser. No. 10/032,657, filed Dec. 28, 2001 can be used, and are incorporated herein by reference. The magnetically responsive material can be also functionalized prior to assembly to provide additional chemical and biological functionality. Alternatively, all sides of a chip can be encoded by randomly adsorbing beads on the chip carrier using methods known in the art. The configuration of the array provides a miniaturized tag identifying the chip ("Chip ID") as well as the wafer of origin ("Wafer ID"). Each ChipID is drawn from the number, S, of distinguishable configurations of a random encoded array of L positions, given by the number of ways in which n (unordered) samples of r (k) (indistinguishable) particles, $1 \leq k \leq n$, may be distributed among L positions:

$$S(L;n;r(k), 1 \leq k \leq n)=L!/[r(1)!r(2)!\ldots r(k)!\ldots r(n)!]$$

Illustrating the large number of possible combinations is the fact that an array of L=16 positions, composed of n=4 distinguishable bead types, each type represented four times $(r(1)=\ldots r(4)=4)$ can display $S(16; 4; r(k)=4; 1 \leq k \leq 4)=16!/[(4!)(4!)(4!)(4!)]$, or approximately 63 million distinguishable configurations.

In using random encoded arrays to produce a number of tags T, where T <<S, for many applications of practical interest, a large configuration space of size S is sampled to reduce the chance for duplication. A particular advantage of constructing tags using random encoded bead arrays is the fact that, by the methods of the present invention, they are readily produced, inexpensively, in miniaturized format and in large numbers in a single process step. ChipID codes in the form of random encoded bead arrays are readily constructed to share common subfields or subcodes which can be used to determine whether two or more chips originated from the same wafer. For example, if a total of n bead types are used to produce ChipIDs for chips on N wafers, p types can be reserved, with p<n and p selected such that $2^p>N$. Wafer-specific subcodes containing only the remaining n-p bead types are then constructed. For example, given n=16 bead types to construct ChipIDs containing a subcode identifying each chip to have originated in one of N=100 wafers, p=7 bead types can be reserved to construct a binary code of 7 digits to identify each of the 100 wafers by the absence of up to seven of the reserved bead types. For example, one of the wafers in the set will lack all 7 of the reserved types, another 7 will lack one of the reserved types. The encoding beads are functionalized and carry probe molecules on their surface. The encoding magnetic particles can also be magnetized and can exhibit chemical and biological functionality.

An example of a fabricated chip is shown in FIG. 4. The substrate is a Si(100), n-type phosphorus-doped wafer with a resistivity of 1.5-4 ohm-cm. The chip is a square with 1.75 mm sides and a thickness of 0.5 mm. Layer L2 is 1000 Å of thermally grown silicon dioxide with a 12-tip star opening in the middle. The dimensions of the star are as indicated in FIG. 4. In the center of the chip, there is an array of closely packed hexagonal recesses comprising 68 rows and 59 columns. The dimensions of the hexagonal recesses are as indicated in FIG. 4. Layer L3 is a 60 Å thick layer of LPCVD silicon nitride, which covers the entire chip except for the sidewalls and bottoms of the hexagonal recesses, where there is only bare silicon with native silicon oxide.

Figure 5:
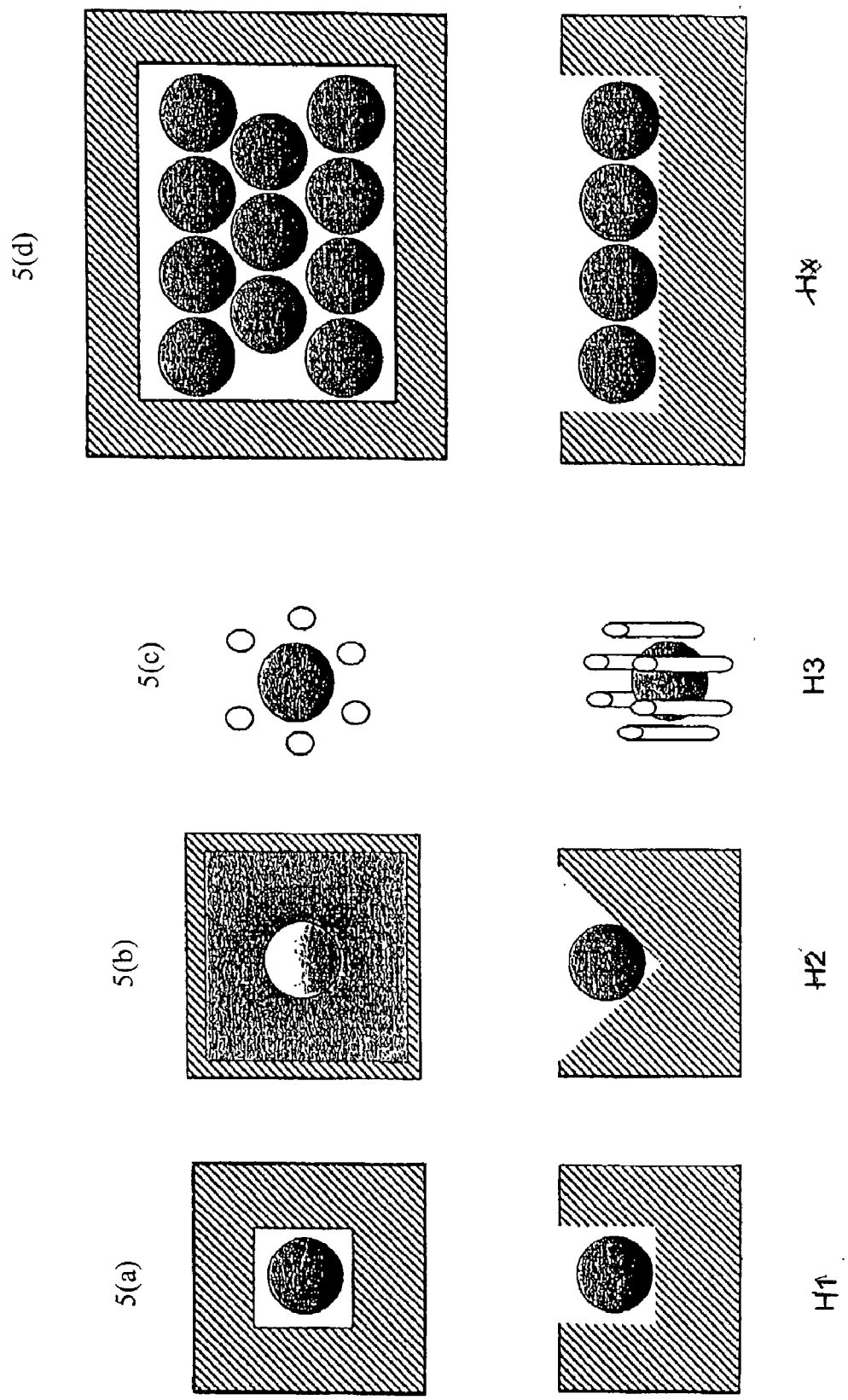
FIG. 5 provides examples of surface structures that can be used to secure beads. H1 is a single-bead retaining hole with straight sidewalls. H2 is a pyramidal recess that can accommodate one bead. H3 is group of posts that confine one bead. Hx is a recess that can hold a plurality of beads.

FIGS. 5*a* and 5*b* illustrate non-limiting examples of other structures suitable for confining the movement of beads. H1 is a single-bead retaining recess or cavity with straight sidewalls. H2 is an inverse pyramidal recess that can accommodate one bead. H3 is group of posts that confine one bead. Hx is a recess that can hold a plurality of beads. The upper drawing (FIG. 5*a*) shows a plan view of the structures, while the lower drawing (FIG. 5*b*) shows a cross sectional view. In one embodiment, a straight side wall compartment H1 that accommodates only one bead can be used. This structure is useful for confining beads in a liquid medium. The shaded area in FIG. 5 is substrate material and the white area is empty space. The compartment shape is not limited to a square; for example a pyramidal recess H2 may be used as a compartment to hold a single bead. Furthermore, although the bottoms of the recesses are preferably flat, they need not be in certain embodiments.

FIG. 6 shows examples of array structures. A1 and A2 are arrays of rectangular recesses. A3 is an array of hexagonal recesses. A multitude of structures can be fabricated on a chip or wafer to form an array or a plurality of arrays on the chip or wafer surface. The structures may be all identical or different types of structures and/or differently sized structures may co-exist. Three illustrative embodiments are illustrated in FIG. 6. In the drawings, the shaded areas are the recesses. The non-shaded areas are the original substrate surface (which may be covered with a thin film). Arrangement A1 is a regular Cartesian array of square recesses. Arrangement A2 is an alternating checkerboard array of square recesses. Arrangement A3 is an array of hexagonal recesses. Although the arrays of this invention are not limited to regular arrays, regular arrays are convenient for interpreting the reaction results.

Figure 10:
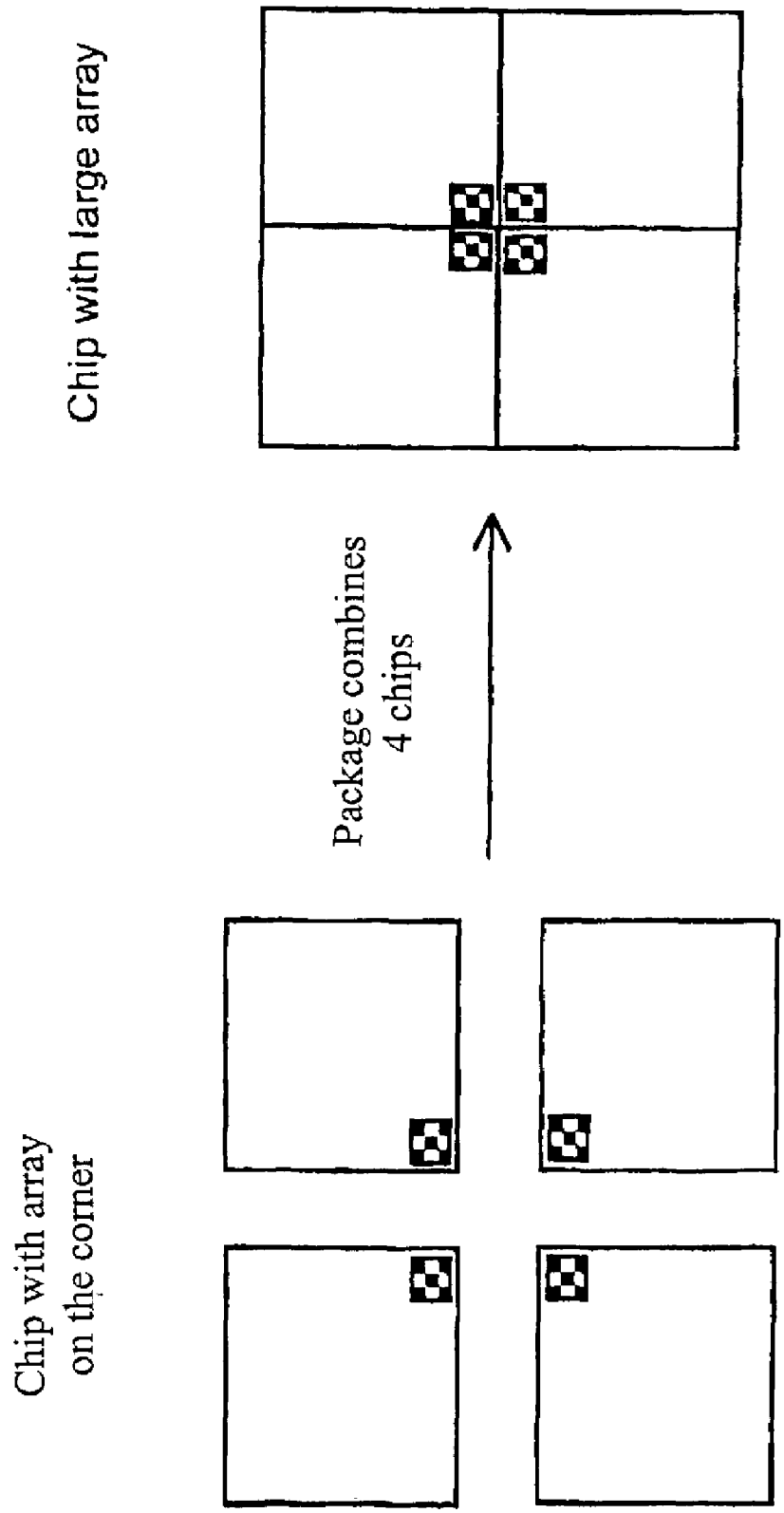
FIG. 10 shows an example of a chip design that sets a probe array on a corner of each chip. By combining four such chips in the way shown in the drawing, a larger array can be formed.

The location of the array on a chip, of course, is not limited to the center. For example, the array can be situated on a corner such as those shown in FIG. 10. In addition there may be more than one array on an chip. For example, four arrays can be fabricated on a single chip as shown in FIG. 10. In some embodiments, different bead groups are added to each of the four arrays on the chip. One method to accomplish this bead distribution in a large-scale process is by using a mask that only exposes one array at a time on each chip. A distinct bead group is added to the exposed arrays. The mask is then shifted to expose another array on each chip and the process is repeated. After repeating four times, each chip will have four arrays with four distinct groups of beads.

1.2 Wafer Fabrication

Several methods can be used to impart a selected chip layout on the wafer using wafer techniques, such as for example photolithography or material etching. The methods selected depend on the wafer design requirements. A wafer undergoes one or more fabrication cycles depending on different requirements to yield a fully fabricated wafer. Each fabrication cycle in this process comprises, but is not limited to, three steps: (i) material growth and/or deposition; (ii) lithography; and (iii) etching. Each cycle usually produces one structural layer. Depending on the target structures on the wafer, one or more layers may be fabricated cycle by cycle.

For example, material growth or deposition can be accomplished by growth of $SiO_2$ on silicon, or chemical vapor deposition of dielectric material such as $SiO_2$, $Si_3N_4$ or others, or deposition of metals such as aluminum, chromium, gold, titanium, or others. The lithography step can include photolithography, e-beam lithography, x-ray lithography, or imprint lithography. The etching step can include the removal of a certain amount of material in certain areas defined by a masking layer, such as, but not limited to, a photoresist. Non-limiting examples of etching methods include anisotropic etching, such as reactive ion etching, crystal plane-biased wet chemical etching, or isotropic etching, such to isotropic wet chemical etching, vapor etching, or plasma etching.

1.3 Wafer Scribing

For the efficiency of functionalization, chip regions are delineated after the wafer fabrication process, so that the chip regions are suitable for batch parallel processing. For this reason, the current invention prefers to scribe the wafer to delineate areas which will give rise following singulation to individual chips. In other embodiments of this invention, chips may be separated using techniques which do not require scribing. The purpose of the scribe lines is to produce lines of breakage to facilitate the separation of individual chips during the wafer singulation step without damaging or breaking the individual chip. It is to be noted that although the scribe line will cede to later breakage, they are sufficiently robust to enable the subsequent steps of the process without breakage of the chips. By way of example, scribe lines can be produced using a wafer scribing machine (e.g. DISCO, Dynatex, or Loomis Industry) to create scribe lines that are only a fraction of the thickness of the wafer. This is followed by the application of a roller in the direction perpendicular to the scribe lines to further delineate individual chips. The wafer can be scribed by using a diamond-tipped scriber; trenches between chips on a silicon wafer can be produced by chemical etching using wet chemicals, such as potassium hydroxide/water solutions at elevated temperature, for example. The wafer can also be dry etched by deep reactive ion etching to yield well-defined trenches between the chips.

1.4 Wafer Cleaning and Inspection

During the step of wafer scribing, dust or particles may be generated. To protect the surface of the wafer, in one embodiment of this invention, a protective layer is applied to the wafer surface. For example, the layer can be in the form of an adhesive tape (if it does not damage the wafer surface), a photoresist coating, or some other organic coating. The protective layer is removed after scribing, by peeling it off the wafer (for example if it is an adhesive tape) or dissolving it in an appropriate solvent. For example, a photoresist layer can be removed by dissolving it in acetone and then rinsing the wafer with isopropyl alcohol. If trace amounts of the protective coating material are left on the wafer, more aggressive cleaning methods can be used. In one embodiment, the wafer is cleaned by an oxygen plasma to remove the trace amounts of organic material. In another embodiment, the wafer is cleaned by the RCA clean, a standard cleaning procedure in the semiconductor industry which involves an ammonium hydroxide/hydrogen peroxide mixture that is heated to about 75° C. In another embodiment, the wafer is cleaned by a mixture of concentrated sulfuric acid and hydrogen peroxide at elevated temperatures (about 60° C.).

1.5 Chip Grouping

Figure 7:
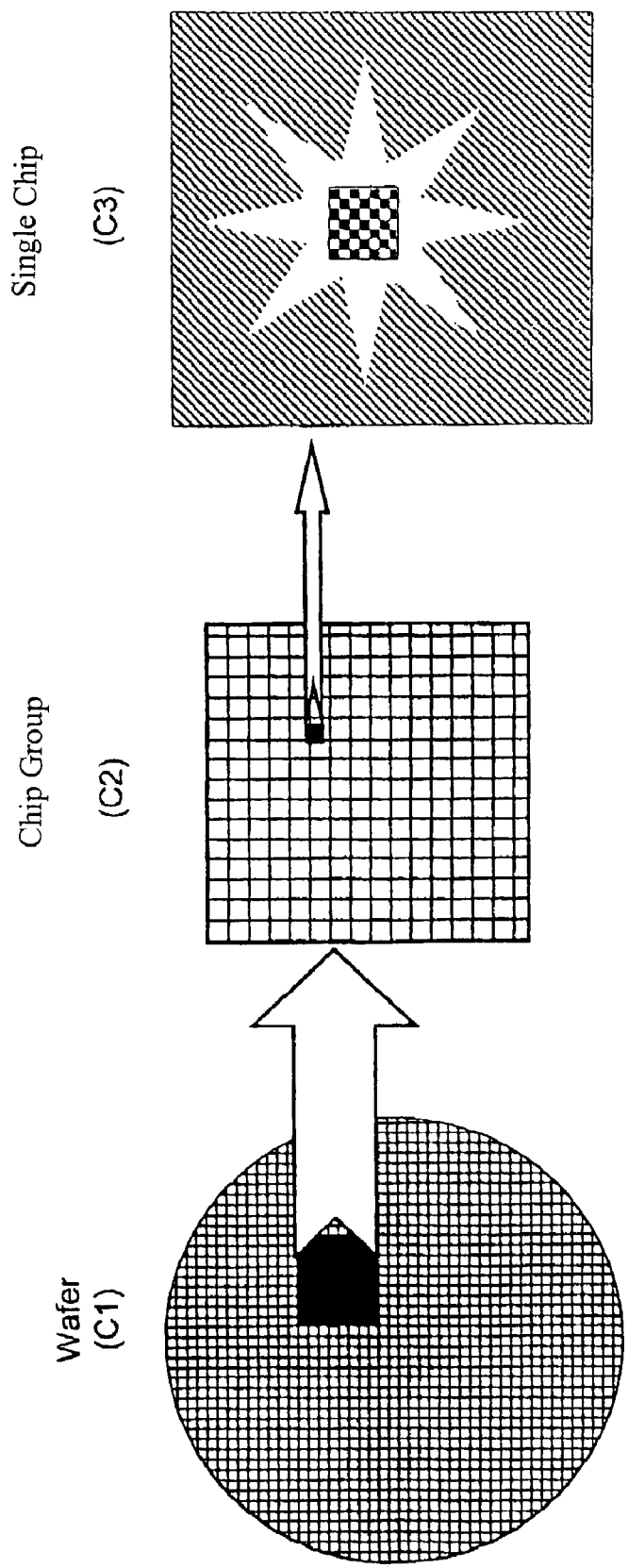
FIG. 7 shows an example of chip grouping.

FIG. 7 shows an example of chip (C3) grouping. C1 is a wafer or any substrate unit that is convenient for batch fabrication such as that used in the semiconductor industry; C2 is a sub-unit of C1 (could be a whole C1) which consists of a desired number of chips; C3 is a chip, which is the smallest unit of a biochip. Usually, C2 is an integrated unit for chip functionalization. After functionalization, C2 is separated into individual C3's.

1.6 Bead Functionalization and Pooling

The terms "microsphere", "microparticle", "bead" and "particle" are herein used interchangeably. The composition of the beads includes, but is not limited to, plastics, ceramics, glass, polystyrene, methylstyrene, acrylic polymers, paramagnetic materials, thoria sol, carbon graphite, titanium dioxide, latex or cross-linked dextrans such as sepharose, cellulose, nylon, cross-linked micelles and Teflon. (See "Microsphere Detection Guide" from Bangs Laboratories, Fishers, Ind.) The particles need not be spherical and may be porous. The bead sizes may range from nanometers (e.g., 100 nm) to millimeters (e.g., 1 mm), with beads from about 0.2 micron to about 200 microns being preferred, more preferably from about 0.5 to about 5 micron being particularly preferred.

In some embodiments of this invention, the beads are functionalized prior to being distributed on the wafer surface, such that each bead has a specific type of biological probe linked on its surface. Various methods for functionalizing the beads are suitable for use with this invention. The appropriate method is determined in part by the nature of the material used to make the bead. For example, beads can be functionalized by attaching binding agent molecules thereto, such molecules including nucleic acids, including DNA (oligonucleotides) or RNA fragments; peptides or proteins; aptamers and small organic molecules in accordance processes known in the art, e.g., using one of several coupling reactions known in the art (G. T. Hermanson, Bioconjugate Techniques (Academic Press, 1996); L. Illum, P. D. E. Jones, Methods in Enzymology 112, 67-84 (1985). In certain embodiments of the invention, the functionalized beads have binding agent molecules (e.g., DNA, RNA or protein) covalently bound to the beads. Beads may be stored in a buffered bulk suspension until needed. Functionalization typically requires one-step or two-step reactions which may be performed in parallel using standard liquid handling robotics to covalently attach any of a number of desirable functionalities to designated beads. Beads of core-shell architecture may be used, the shell composed in the form of a thin polymeric blocking layer whose preferred composition is selected; and functionalization performed in accordance with the targeted assay application.

In some embodiments of this invention, the beads are color-coded with fluorescent dyes. For use in various assays, the beads may comprise additional dye-tagged biological substances on their surfaces. To detect the signal of the beads and assay, fluorescent microscopic imaging can be used.

A bead library is established by preparing subpopulations of different groups of beads. Each bead subpopulation is prepared by affixing one type of molecular probe from a probe library to a plurality of beads, forming the subpopulation. Each bead subpopulation is distinguishable by color coding with fluorescent dye or other method.

II. Assembly

Bead arrays are assembled by securing beads on the surface of a wafer or portion of wafer. Prior to securing the beads a wafer surface; a bead library can be formed by chemical encoding or staining of beads with sets of optically distinguishable tags, such as those containing one or more fluorophore dyes spectrally distinguishable by excitation wavelength, emission wavelength, excited-state lifetime or emission intensity. The optically distinguishable tags made be used to stain beads in specified ratios, as disclosed, for example, in Fulwyler, U.S. Pat. No. 4,717,655. Staining may also be accomplished by swelling of particles in accordance with methods known to those skilled in the art, (Molday, Dreyer, Rembaum & Yen, J. Mol Biol 64, 75-88 (1975); L. Bangs, "Uniform Latex Particles, Seragen Diagnostics, 1984]. For example, up to twelve distinguishable populations of beads can be encoded by swelling and bulk staining with two colors, each individually in four intensity levels, and mixed in four nominal molar ratios. Combinatorial color codes for exterior and interior surfaces are disclosed in International Application No. PCT/US/98/10719, which is incorporated herein by reference in its entirety. Color codes are also discussed in U.S. Pat. No. 6,327,410, which is hereby incorporated by reference in its entirety.

There are many possible ways to secure beads on the surface of a chip when forming bead arrays. Recesses that are formed during wafer fabrication steps provide compartments that retain the beads on the surface of the substrate. The effectiveness of securing (or immobilizing) the beads depends on the dimensions of the recess relative to the size of the bead. Dimensions of recesses used for this purpose are such that the depth of the recess is about 0.5 to 1.5 times the diameter of the beads used. More preferably, the dimensions of the recess are such that when a bead is gravitationally stable in the recess, its highest point is below the top of the edges, and there is only sufficient room to accommodate up to ⅓ the volume of another bead. In addition, while it is preferred that the size of the recess is greater than the size of the bead, in this preferred embodiment, each recess should not be capable of accommodating more than one bead. Further, the openings of the recesses are slightly larger than the beads. The hexagonal array shown in FIG. 4, for example, is compatible with beads having a diameter of 3.2 microns.

It may not be necessary to use recesses in a substrate to hold the beads. For example, a plurality of posts can be arranged on a substrate surface to restrain the beads. A possible structure is shown in the upper drawing (plan view) and in the lower drawing (perspective view) of FIG. 5c. In this case, each bead is confined by six posts around it. The number of posts is not limited to six, but could be three or more. Furthermore, any other raised or lowered surface structure, including blocks, posts, bumps, and indentations may be used. In other embodiments, large recesses capable of holding more than one bead may be used. For example, FIG. 5d shows a large recess with straight side walls. The overview in the upper drawing shows that the horizontal dimensions of the large recess are more than twice that of a bead diameter.

As described above, the geometry and size of the recesses used in the assembly of micro-particle arrays can be varied. In certain embodiments, the geometry and size are varied by depositing a layer of silicon oxide or polymer after the holes are formed by etching. For example, recesses with re-entrant sidewall profiles can be formed by this deposition process. In this context, the term "re-entrant sidewall profile" refers to the situation where the sidewall profile is such that the diameter of the recess opening at the surface is smaller than the diameter of the recess at its bottom. Recesses with re-entrant sidewall profiles formed by this method have a higher bead retention rate during processing and assaying.

Beads may be affixed to a surface by covalent bonds or by van der Waals, electrostatic, gravitational, magnetic or other forces. Combinations of such bonding methods may also be used. In one embodiment, bead arrays can be produced by picking aliquots of designated encoded beads from individual reservoirs in accordance with the specified array composition. "Pooled" aliquots of suspension are dispensed onto selected substrates such as a wafer delineated into compartments.

In other embodiments, the bead array can be prepared using LEAPS. In these embodiments, a first planar electrode that is substantially parallel to a second planar electrode ("sandwich" configuration) is provided, with the two electrodes being separated by a gap containing an electrolyte solution. The surface or the interior of the first planar electrode is patterned by an interfacial patterning method, as described below. Encoded and functionalized beads are introduced into the gap. When an AC voltage is applied to the gap, the beads form a random encoded bead array on the first electrode (e.g., a chip or a wafer). Alternatively, an array of beads may be formed on a light-sensitive electrode e.g., chip or wafer) using LEAPS. Preferably, the sandwich configuration described above is also used with a planar light sensitive electrode and another planar electrode. Once again, the two electrodes are separated by a gap that contains an electrolyte solution. The functionalized and encoded beads are introduced into the gap, and upon application of an AC voltage in combination with a light, they form an array on the light-sensitive electrode.

Substrates (e.g., chips or wafers) used in the present invention may be patterned in accordance with the interfacial patterning methods of LEAPS by, for example, patterned growth of oxide or other dielectric materials to create a desired configuration of impedance gradients in the presence of an applied AC electric field. Alternatively, a patterned substrate may be obtained by selectively doping interior regions of the substrate. Patterns may be designed so as to produce a desired configuration of AC field-induced fluid flow and corresponding particle transport. Substrates may be patterned on a wafer scale by using semiconductor processing technology. In addition, substrates may be compartmentalized by depositing a thin film of a UV-patternable, optically transparent polymer that affixes a desired layout of fluidic conduits and compartments to the substrate to confine a fluid in one or more discrete compartments, thereby accommodating multiple samples on a given substrate.

Spatial encoding, for example, can be accomplished within a single fluid phase in the course of array assembly by, for example, using LEAPS to assemble planar bead arrays in any desired configuration in response to alternating electric fields and/or in accordance with patterns of light projected onto the substrate. LEAPS creates lateral gradients in the impedance of the interface between silicon chip and solution to modulate the electrohydrodynamic forces that mediate array assembly. Electrical requirements are modest: low AC voltages of typically less than $10V_{pp}$ are applied across a fluid gap of typically 100 m between two planar electrodes. This assembly process is rapid and it is optically programmable: arrays containing thousands of beads are formed within seconds under an electric field. The formation of multiple subarrays, can also occur in multiple fluid phases maintained on a compartmentalized chip surface. Alternatively, spatial encoding is accomplished by assembling separate chips, each carrying at least one random encoded array drawn from a specific pool, into designated multichip configurations.

In one embodiment, the process disclosed in PCT/US01/20179, incorporated herein by reference in its entirety (the process referred to as "READ"), can be used to prepare custom bead arrays which can be used in performing multiplexed biomolecular analysis according to the present invention. Using READ, the array can be prepared by employing separate batch processes to produce application-specific substrates (e.g., chip at the wafer scale) and to produce beads that are chemically encoded and biologically functionalized (e.g., at the scale of ~$10^8$ beads/100 1 of suspension). Preferably, the beads are subjected to respective quality control (QC) steps prior to array assembly, such as the determination of morphological and electrical characteristics, the examples of the latter including surface ("zeta") potential and surface conductivity. In addition, actual assays are performed on beads in suspension before they are introduced to the substrate. This is to optimize assay conditions, generally with the objective of maximizing assay sensitivity and specificity and to minimize bead-to-bead variations. For substrates, QC steps may include optical inspection, ellipsometry and electrical transport measurements.

Once the chemically encoded and biologically functionalized beads are combined with the substrate (e.g., chip or wafer), LEAPS or another active deposition process described herein allows rapid assembly of dense arrays on a designated area on the substrate. By assembling within the same fluidic phase, problems such as spot-to-spot or chip-to-chip variability are avoided without the need for retooling or process redesign. Furthermore, the uniformity of these processes allow for chip-independent characterization of beads as well as optimization of assay conditions. In addition, multiple bead arrays can be formed simultaneously in discrete fluid compartments maintained on the same chip or wafer. Once formed, these multiple bead arrays may be used for concurrent processing of multiple samples. The integration of LEAPS with microfluidics produces a self-contained, miniaturized, optically programmable platform for parallel protein and nucleic acid analysis.

Once the functionalized and encoded beads are prepared and then combined with the substrate, the binding interaction between the binding agent on the beads and an analyte may be performed either before or after the random encoded array is assembled on the substrate. For example, the bead array may be formed after the assay, subsequent to which an assay image and a decoding image may be taken of the array. Alternatively, the beads may be assembled in an array and immobilized by physical or chemical means to produce random encoded arrays. A DC voltage may be applied to produce random encoded arrays. The DC voltage, typically set to 5-7 V (for beads in the range of 2-6 m and for a gap size of 100-150 m) and applied for <30s in "reverse bias" configuration so that an n-doped silicon substrate would form the anode, causes the array to be compressed, facilitating contact between adjacent beads within the array and simultaneously causes beads to be moved toward the region of high electric field in immediate proximity of the electrode surface. Beads can be anchored on the surface by van der Waals forces or "tethers" extending from the bead surface, e.g. polylysine and streptavidin.

After bead assembly, the chips or wafers are inspected and are imaged by fluorescent microscopy to obtain a decoding map. The decoding can be later used identifying the position and functionality of each individual bead.

The percentage of the array positions that are filled is preferably higher than 50%, more preferably higher than 90%. To test how effectively the recesses retain the beads at the surface of the substrate, chips comprising bead arrays were placed in an aqueous solution and were continuously shaken for three days. A comparison of the images taken before and after this test revealed that over 99% of the beads on all of the tested chips remained in the recesses.

III. Post-Assembly

During post-assembly, the bead arrays may be covered with a protective surface. Before or after covering the beads, the wafers comprising the bead arrays are singulated into one or more bead chips.

3.1 Securing of Microparticles

In certain embodiments of the invention, a gel covering the bead array area can be used to prevent the beads from dislodging. In other embodiments, chemical functional groups on the bottoms and/or the sidewalls of the recesses can be used to link the beads to the surface. A charged polymer can also be used to coat the chips prior to bead deposition. The charge of the polymer coating is chosen to be opposite to that of the beads, so that the beads will be electrostatically attracted to the polymer. When a bead is in a charged polymer-coated recess, the Coulombic attraction between the bead and the sidewalls and bottom of the recess serves to hold the bead in the recess. In this way, the bead retention rate during processing and assaying is increased. In some embodiments, a second charged polymer is deposited on the chip surface after beads have been placed in the recesses. The charge of the second polymer is chosen to be the same as that of the bead, so that no polymer is deposited on the bead, but the surface charge on the chip is neutralized. Several variants of this techniques can be implemented with minimal alteration of the core process. For example, a single polyelectrolyte layer may be used, or a multi-layered structure (having alternating positive and negative polymer layers) can be constructed to yield a coating with a more uniform and controlled thickness. Further, instead of polymers, charged polymer nanoparticles alone or in combination with charged polymers can also be used. An uncharged but low $T_g$ (glass transition temperature) polymer and/or nanoparticle coating can also be used to improve the adhesion of the beads to the chip surface.

3.2 Protection of Assembled Arrays

Removable coatings can be used to protect the bio-functionalized beads in the arrays of either a wafer before singulation into biochips or the singulated biochips themselves. It is desirable therefore to have a way to protect the bead array from ambient dust, dirt, and other contaminants while the biochip or wafer is in storage. This invention provides protective coatings for biochips and wafers and methods of preparing such coatings. In preferred embodiments, the coatings protect the beads in bead arrays from ambient contamination and prevent the degradation of the bio-molecules (e.g. probes) on the surface of the beads. Further, the coatings can be easily removed from the surface of the biochip prior to performing bioassays.

In certain embodiments, the coating comprises an inert, non-reducing sugar, such for example trehalose. which does not interact with reactive chemical moieties such as amino groups in peptides and proteins, and thus prevents the degradation or aggregation that is common when drying with other excipients.

In other embodiments, a hydrogel (e.g., an agarose hydrogel) may be used to prevent contamination, dehydration, and physical damage during storage. Prior to performing a bioassay, the hydrogel may be peeled from the substrate surface. The act of peeling not only removes the hydrogel, but also cleans the surface of any extra beads that are not in array positions defined by recesses or other restraining structures. These extra beads, which are embedded in the hydrogel, can be recovered for further use.

3.3 Chip Singulation

After functionalization, the chip groups (wafer or subunit of a wafer) are singulated. If the wafer was previously scribed, it can be singulated by breaking the connections between the chips. This can be done by rolling a roller on the back of the wafer in the direction perpendicular to the scribing lines, in accordance with the procedure outlined in U.S. Pat. No. 3,790,051. Alternatively, singulation can be achieved by other methods such as using the GST Scriber/Breaker manufactured by Dynatex International™. The individual chip obtained this way are ready for packaging. In addition to the singulation methods described herein, any other method of singulation, such as for example laser cutting, can also be used to achieve the objectives of the invention.

In some embodiments, the wafer or subunit is singulated prior to bio-functionalization. The individual chips can then be bio-functionalized identically or bio-functionalized by exposing subpopulations of the chips to different bioactive groups.

IV. Packaging

Figure 15A:
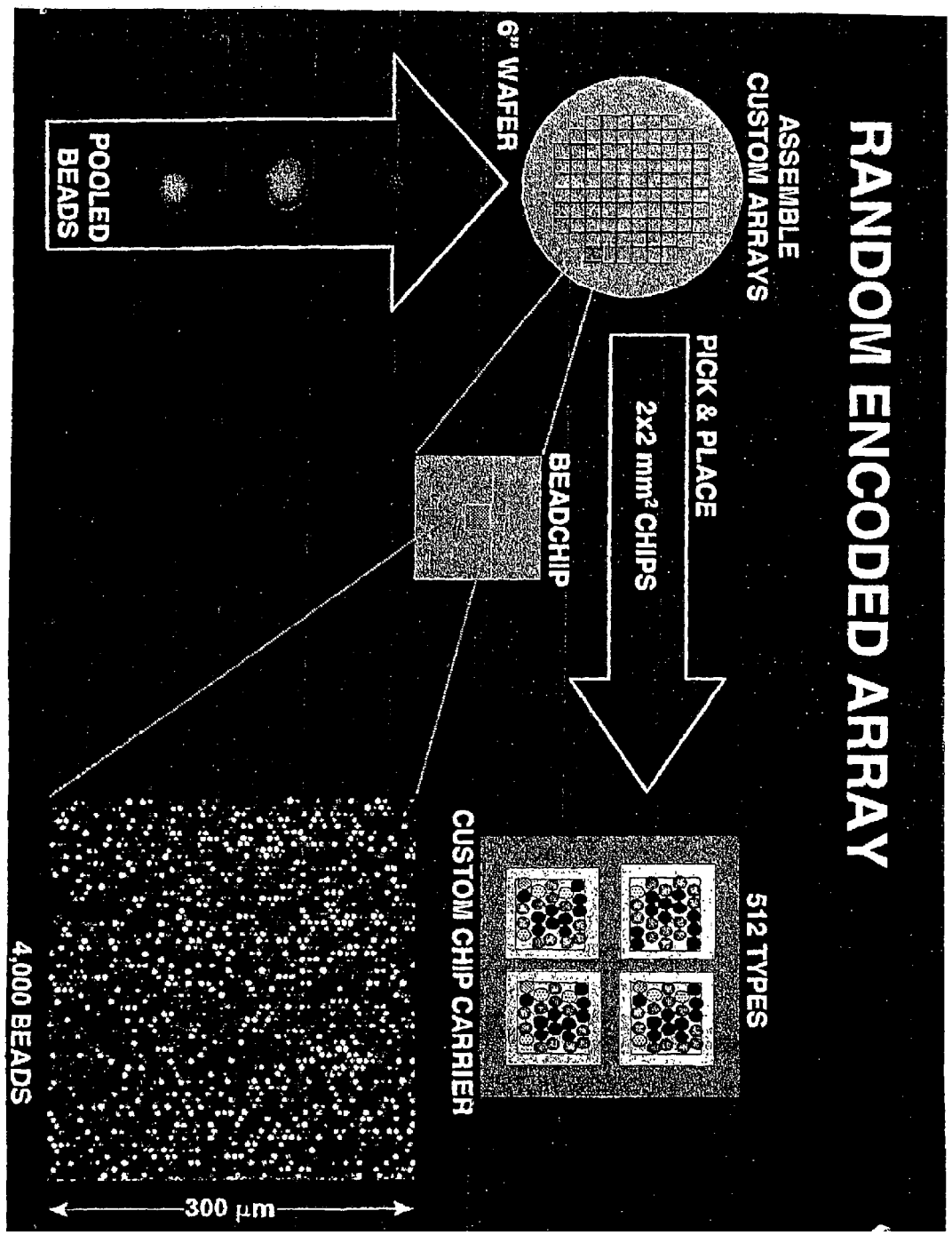
FIG. 15(a) illustrates an example of a random encoded array.
Figure 15B:
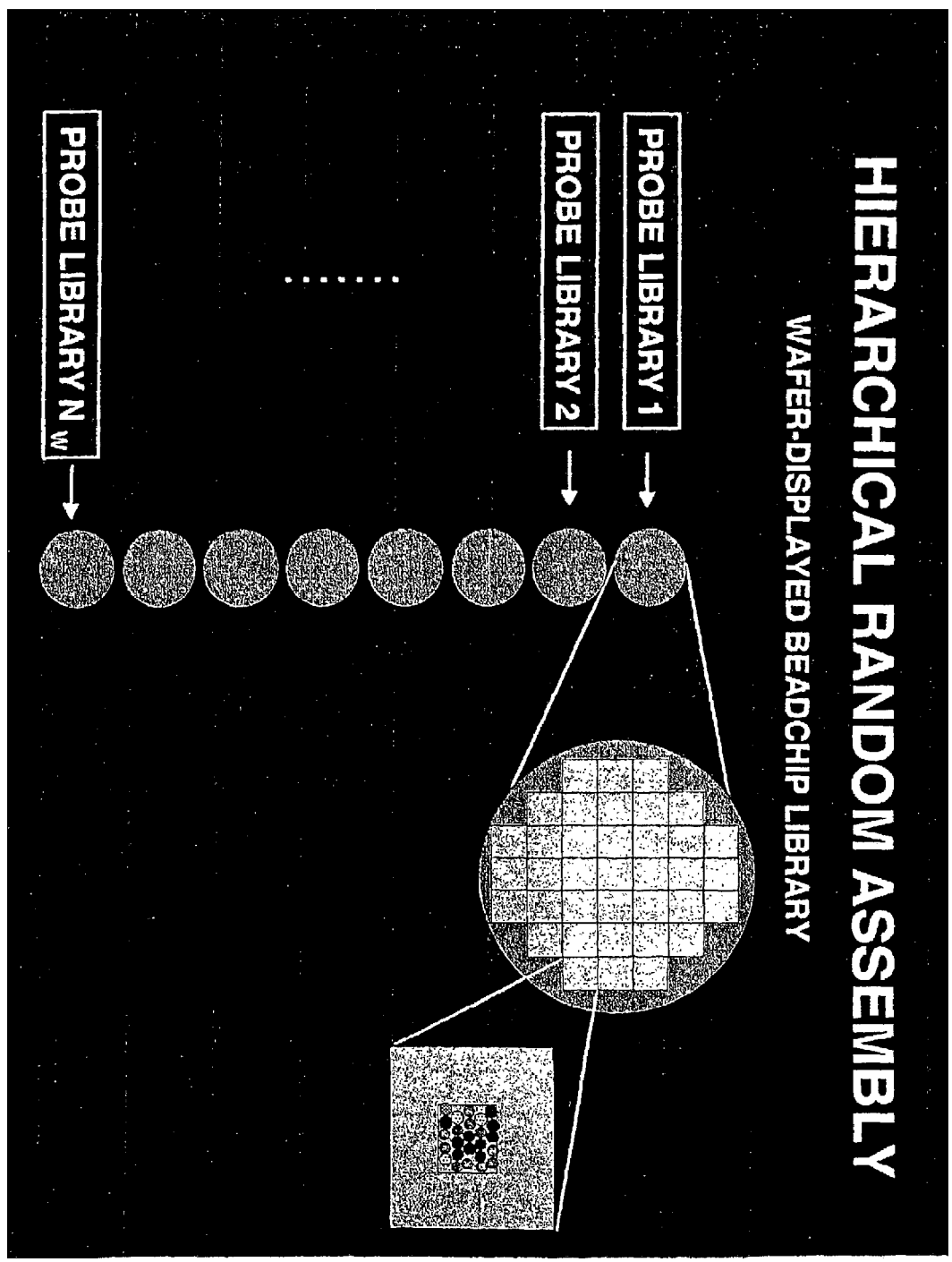
FIG. 15(b) illustrates an example of a library of chips.
Figure 15C:
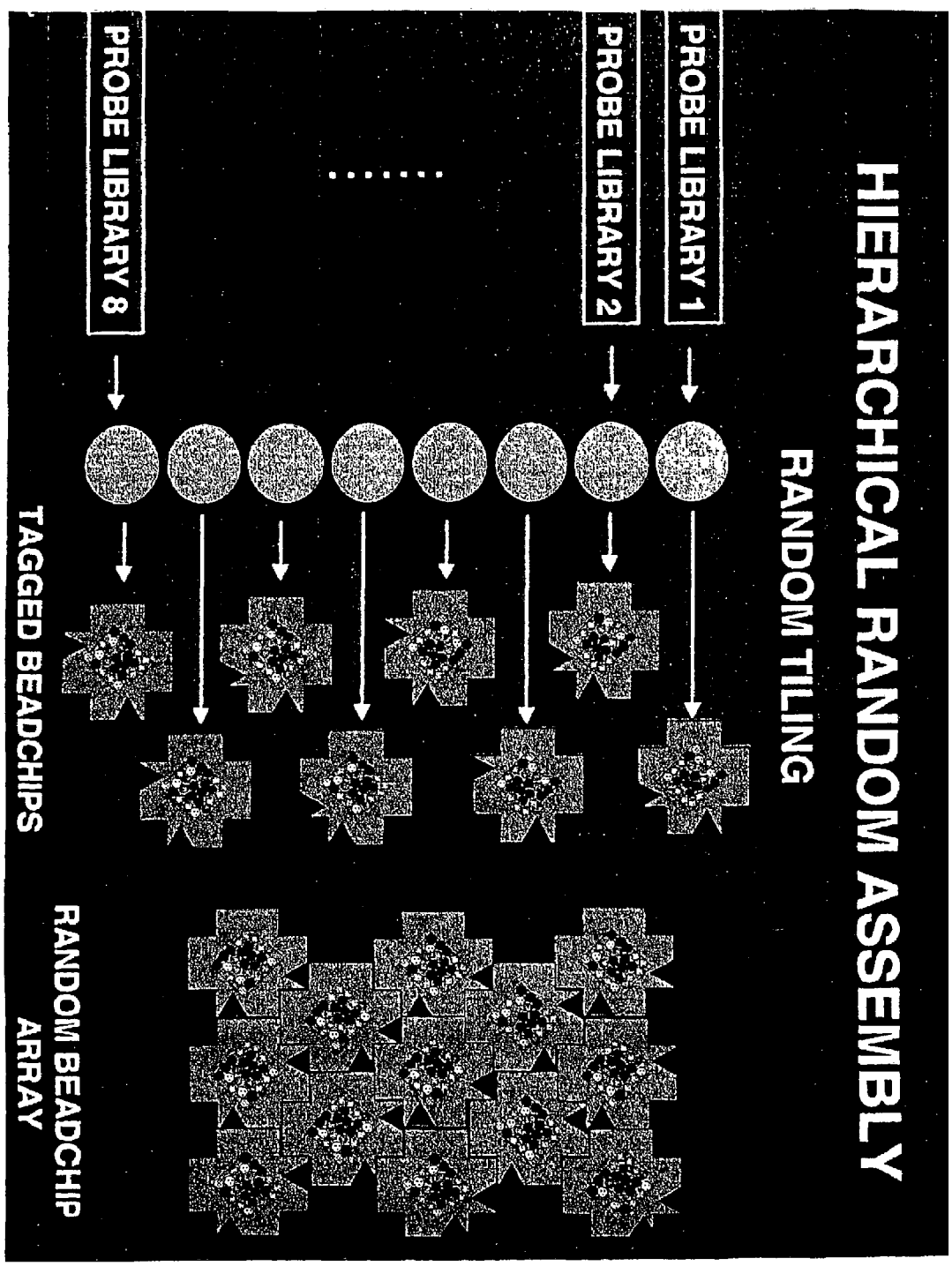
FIG. 15(c) illustrates an example of a random assembly of chips from the library of chips.
Figure 15D:
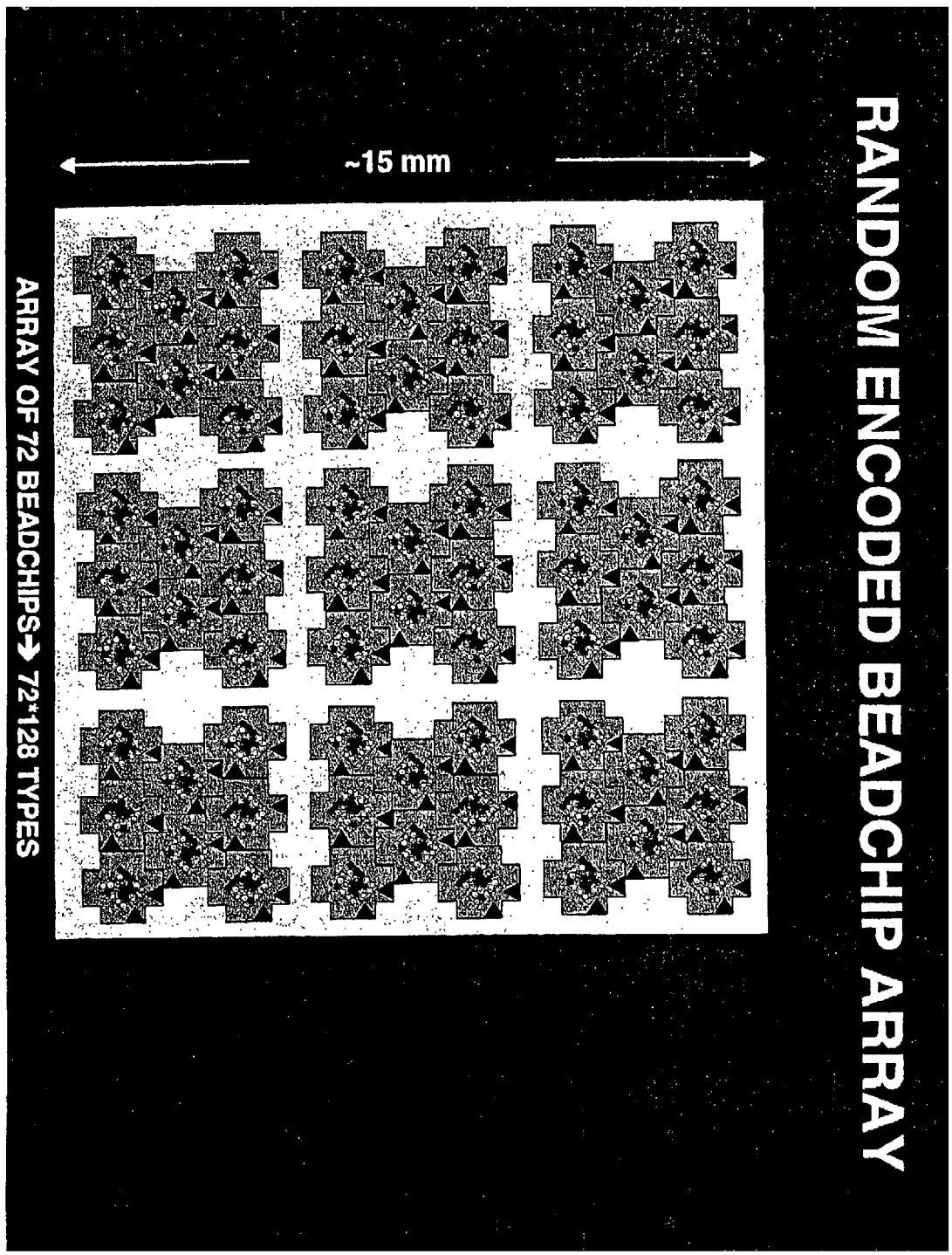
FIG. 15(d) illustrates an example of random tiling of array
Figure 16:
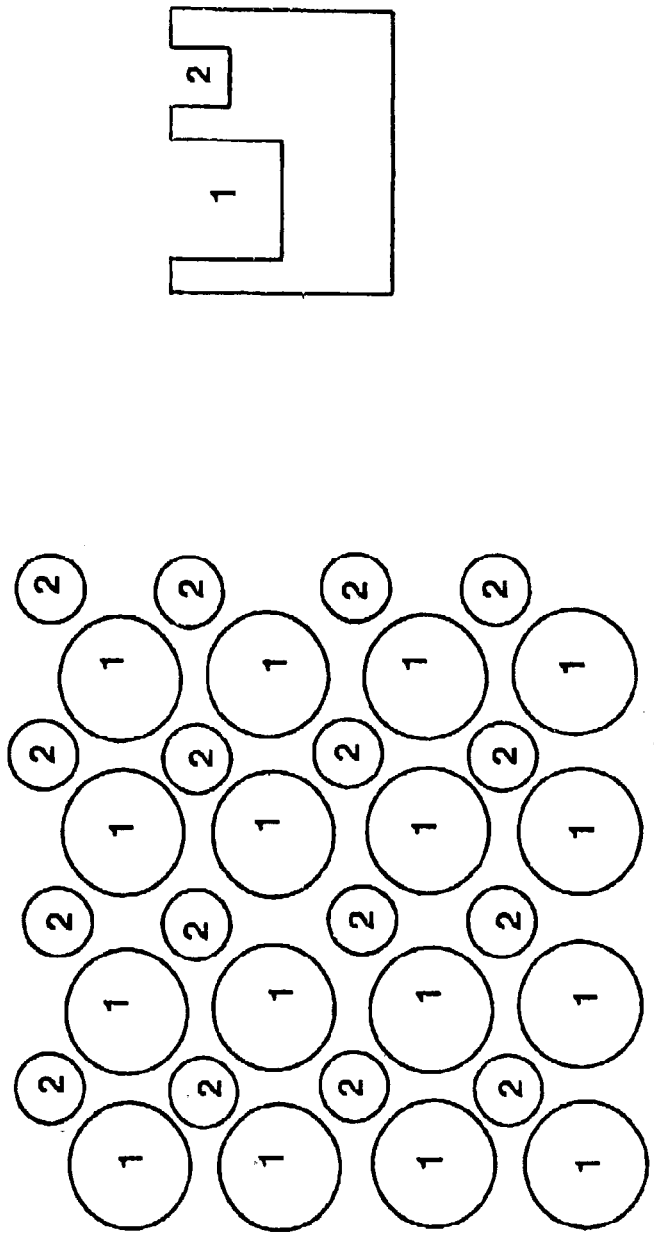
FIG. 16 is an illustration of array design for simultaneous assembling or sequential assembling of groups of beads with distinct sizes.
Figure 17:
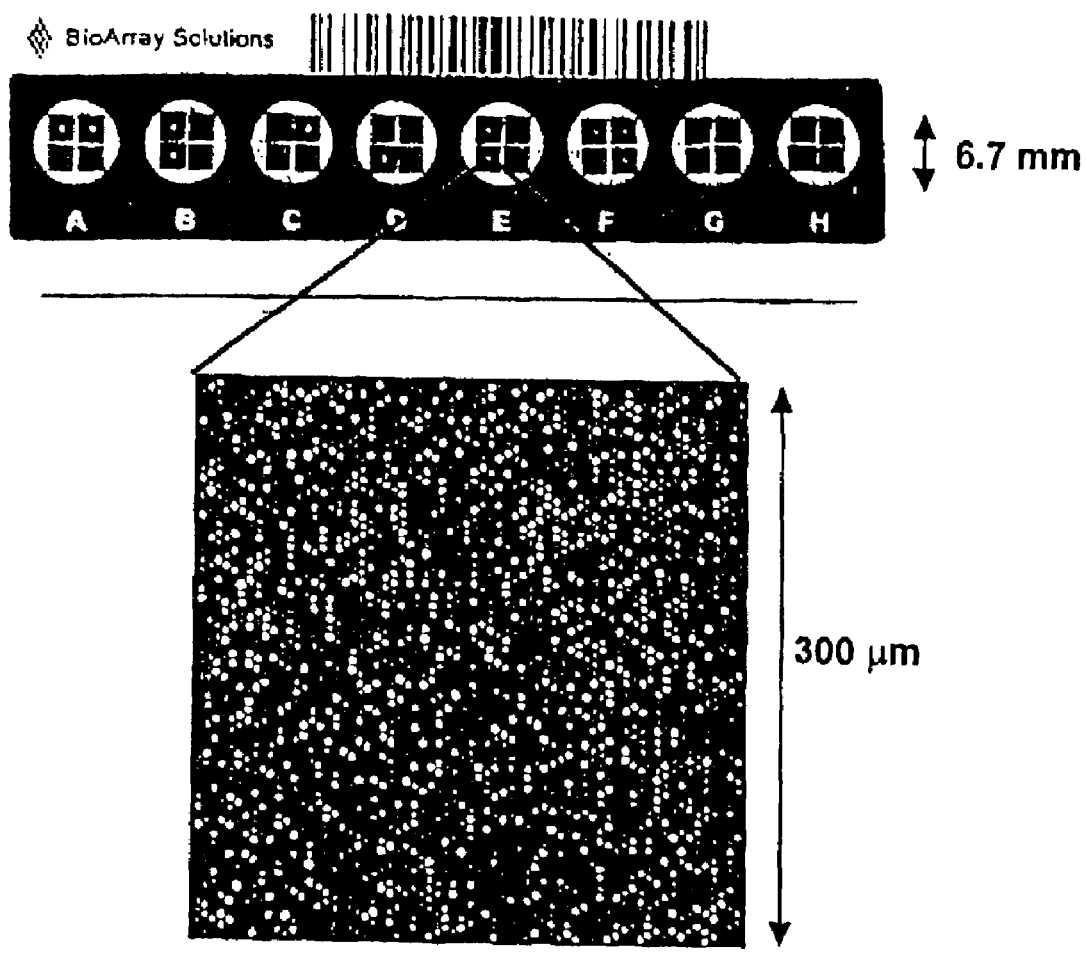
FIG. 17 is an illustration of multichip carrier design.

Using the methods of the present invention, a multiplicity of chips can be produced by the assembly of random encoded arrays of probe molecules displayed on encoded beads. Each chip, cut from a uniquely identified wafer, may contain one or more random encoded bead arrays. It is possible to generalize This method of random assembly according to the invention encompasses an embodiment wherein the bead-displayed probes on chips containing random encoded arrays are members of large probe libraries that are displayed on tagged chips selected from a multiplicity of wafers. Chips from different wafers may be selected and assembled to form pooled chip sets. Preferably, chips display a decodable tag identifying the wafer of origin. Arrays of encoded chips may be formed by random assembly on a planar surface in a process also referred herein as random tiling, illustrated in FIG. 15d. Random tiling refers to a process of assembling a set of encoded chips into a planar arrangement or array so as to permit optical inspection of each chip or part of each chip within the assembly or array.

This hierarchy of scales for random assembly, from the bead array level to the chip array level provides flexibility for quickly creating arrays of large probe sets of customized composition and high feature density. Such arrays could be used for displaying a large set of probes for gene expression profiling, or for profiling the methylation of DNA by assay methods known in the art. In addition, when it is desirable to expose multiple probe arrays to separate reactions, a random tiling process of affixing a plurality of chips on a single support as discussed below, provides a rapid and flexible novel approach to implement pooling and deconvolution strategies known in the art For example, arrays displaying partially overlapping probe sets are readily produced by suitable construction and selection of chips.

Figure 14:
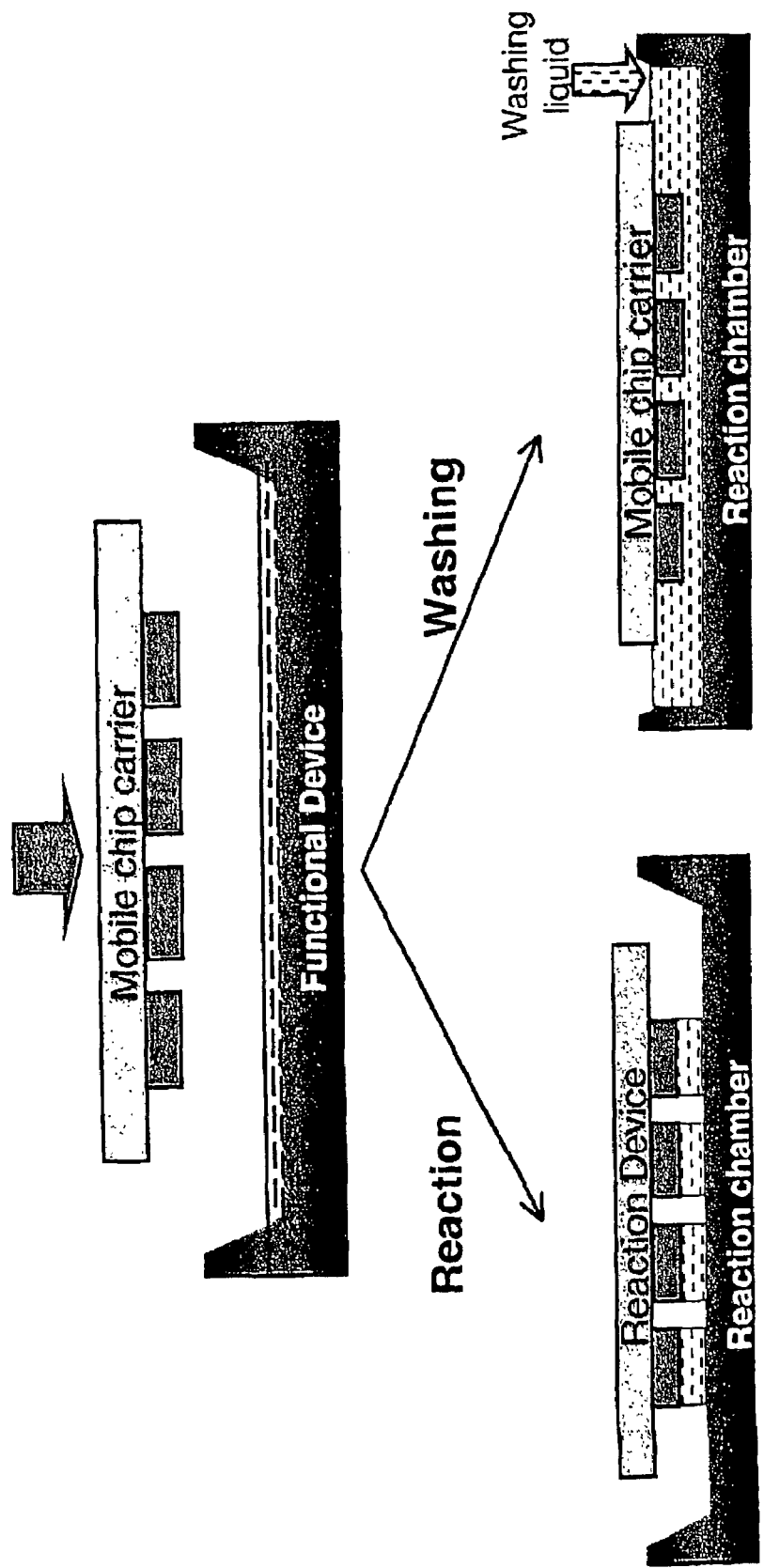
FIG. 14 is an illustration of a mobile chip carrier and its application in conjunction with reaction chambers.

Following the assembly of the bead arrays of this invention, wafers are singulated to permit manipulation of individual tagged chips. In random tiling, tagged chips that are selected from one or more wafers are placed onto a surface (preferably provided by a flat substrate) on which chips can be moved about to form a multi-chip assembly corresponding to a desired layout. To facilitate close packing, chips may be designed to display a convex symmetric shape such as a square, triangle or hexagon. To decrease the distance between bead arrays on adjacent chips, chips may be designed to display interlocking shapes (FIG. 14c).

Sliding Assembly

In this embodiment, multiple singulated wafers are placed onto a common large substrate with the sides displaying the probe arrays facing down. In preferred embodiments, the probe arrays are recessed to prevent direct contact with the substrate. One or more chips are randomly selected from each wafer and, in a manner similar to sliding coins on a table top, arranged to form a chip array by sliding the chips into a designated assembly area. This process may be generalized to row-and-column manipulation shown in FIG. 8. In this embodiment, the tiling process can be monitored and recorded by standard optical and machine vision instrumentation available for semiconductor inspection. This instrumentation can be used to track chips from their respective wafers of origin to their respective final positions, permitting direct positional encoding and decoding of the assembled chip array. Following completion of the assembly process, a multi-chip carrier (as described herein) is aligned with one or more chip arrays arranged in the assembly area and then lowered and bonded to the chips to form a multichip assembly. To facilitate bonding, carriers may be pre-coated with adhesive or may be coated with magnetic materials, if the chips are rendered magnetizable by methods described herein.

This method of sliding assembly preferably uses a mechanical tip, such as a suction device capable of lifting and handling individual chips as known in the art. Alternatively, magnetizable chips are manipulated using a magnetic stylus capable of selecting one or more chips from each wafer. Wafers (and chips contained thereon) may be rendered magnetizable by the deposition of a magnetic material such as nickel or a nickel-iron alloy ("permalloy") by electroplating or electroless deposition, as understood in the art for example for semiconductors and ceramics. Alternatively, paramagnetic microparticles may be introduced, either as a part of the random encoded arrays of microparticles displaying probe molecules or as a separate feature, for example in the form of an array assembled in a designated portion of each chip. The array of magnetizable particles may be on the side of the chip containing the random encoded probe array or on the opposite side.

Sliding assembly generally involves handling of individual chips and becomes increasingly cumbersome as the number of constituent chips in a chip array increases. This situation is exacerbated if the chips are small, displaying for example, linear dimensions of 100 μm or less. For example, small chips of cubic or near-cubic shape may be formed in this dimension from ceramic substrates. In these situations, the individual chips are best handled by methods known in the art for the handling of glass or polymer microparticles of similar dimensions.

Collective Assembly

In this embodiment, chips that are cut from individual wafers are stored in bulk suspension using an inert storage buffer such as high purity water containing a trace amount of azide. The chips are suspended by mechanical or magnetic agitation. Pools of chips are formed by dispensing and mixings aliquots of selected suspensions. Optionally, a trace amount of glucose or other high soluble, molecular weight ingredient may be added to this suspension to increase viscosity and thereby improve the flow characteristics. The suspension is then deposited on a planar substrate either by spotting discrete aliquots using a syringe, pipette or capillary to achieve random deposition or by using continuous methods known in the art to produce arrays of colloidal particles including those invoking the action of flow and capillary forces [Adachi, E., et al, Langmuir, Vol. 11, 1057-1060 (1995); Science, Vol. 276, 233-235 (1997)].

In the case of random deposition, a template can be provided on the substrate to guide the placement of individual chips and to contain them in designated positions on the substrate. In one embodiment, chips may be collected from the mixed suspension by inserting a mesh into the suspension and retracting it, such that the individual chips are literally lifted or "scooped" out. Preferably, chips, particularly when placed on a flat, feature-free substrate, are separated from one another sufficiently so as to prevent partial overlap and stacking before they are "racked up" into a close packing configuration. Separation is achieved, for example, by sliding assembly (see above) or by mechanical agitation that takes advantage of inducing "drum modes" on flexible substrates such as polymeric substrates, as practiced in the art.

In a preferred embodiment, chips are "racked up" by mechanical means, for example by entraining chips in a fluid flow directed parallel to the substrate surface in a sandwich flow cell in which chips forced against a barrier at the far end of the flow cell.

Preferably, chips within a random assembly are oriented so as to expose the active side displaying random encoded probe arrays. In cases where the active side is not exposed, the chips must be inverted. Inversion of chips into the preferred orientation is achieved by cycles of mechanical agitation and bonding of correctly oriented chips (coated with a heat or light-activated bonding adhesive). Alternatively, inversion during mechanical agitation is aided by displacing the center of mass toward the undesired side of the chip, for example by metallization. Magnetizable chips can be deposited in the presence of magnetic field gradient aligned perpendicularly to the substrate surface providing for sufficiently slow settling in a high viscosity medium to permit chips to adopt the correct orientation as they approach the surface.

Inversion also is facilitated by producing three-dimensional shapes, such as a pyramidal shape, the tip of the pyramid facing away from the active surface, as produced by standard semiconductor etching methods.

Figure 8:
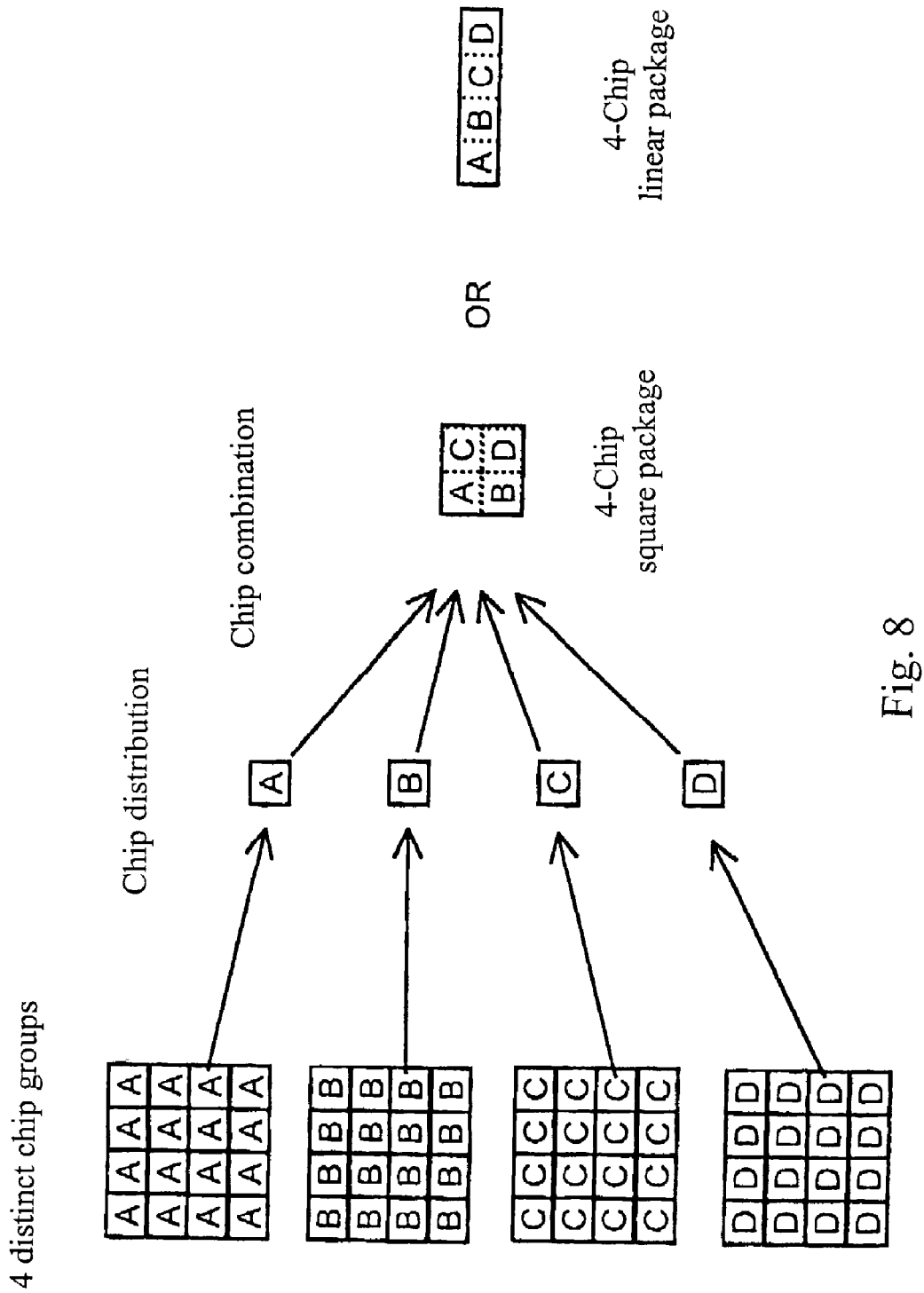
FIG. 8 illustrates the process of chip packaging. A, B, C, D are chips with different functionalization. Wafers can be separated into chips by breaking the wafer according to the scribing lines. Individual chips with different functional groups which were separated from different wafers can be placed together. A 4-chip package consists of four distinct functionalized chips bonded next to each other for biological application. The four chips can be arranged in a variety of ways, with non-limiting examples including square or linear formats.
Figure 9:
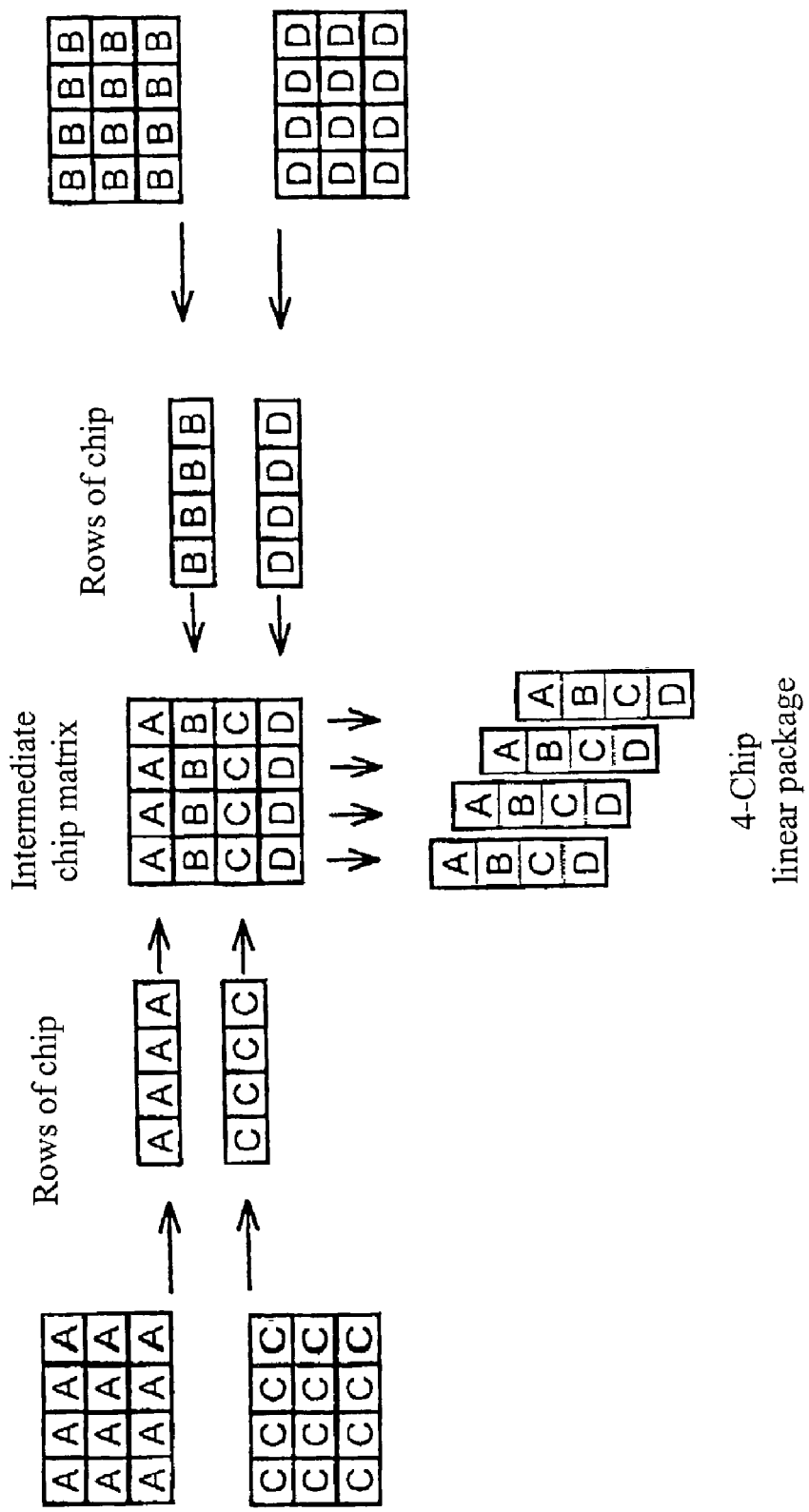
FIG. 9 illustrates a method of assembling chips by moving free chips in rows and columns.

The chips can be packaged in single or multi-chip packages. In a multi-chip package, chips containing different bioprobe arrays are placed on the same carrier. FIG. 8 shows four chips packaged together to form a square combo chip or a linear combo chip. The four chips can be glue-bonded to a common carrier such as a glass slide, or they can be attached to a carrier by other methods, such as bonding magnetic materials on the back of the chips so that they stick to a magnetic carrier. The chip handling is not limited to using pick-and-place equipment. The chips can be grouped in rows or columns after singulation. These rows and columns of chips can be moved by confinement bars. FIG. 9 shows that by selectively arranging different chip rows, different combinations of chips can be obtained.

Another package design is shown in FIG. 10. Four chips with arrays on the corners can be combined to form a chip with a larger array in the middle. If the arrays on the four chips comprise distinct functional probes, the big array will contain four times as much information as a single chip.

A multiplicity of chips can be produced by the assembly of random encoded arrays of probes that are displayed on beads. Each chip may include one or more random encoded bead arrays and may be cut from a uniquely identified wafer. In another embodiment, chips containing random encoded arrays of probes on beads can be members of probe libraries. In this embodiment, each chip in a multichip array displays a decodable tag that identifies the wafer of origin.

A glass surface in the form of a slide or other similar surface may be used to make a multichip carrier. To prepare the slide as a carrier, a coating, such as Teflon™, may be applied in such a manner as to leave circular openings or wells (i.e., areas of glass without any Teflon covering). Each well is a circle with 6.5 mm in diameter. One or more chips can be bonded to the glass surface within a well. A typical glass slide is 25×75 mm and 1 mm thick, with a 2×5 array of wells. With typical chip sizes of 1.75×1.75 mm, up to four chips can be bonded to the glass surface in each well. Each chip in the same well can have distinct bead groups that were assembled prior to bonding to the carrier. For example, if each chip has an array containing 39 types of bead groups, a well with 4 distinct chips would have a total of 4×39=156 types of beads. On the other hand, for larger chips (e.g., a 4.5×4.5 mm square) an entire well is occupied by a single chip. For the well dimensions described herein, each well can hold up to 40 μl of liquid (usually an aqueous solution). Typically, a 20 μl volume of sample solution is added to each well for biological reactions, such that each chip is totally covered by the sample solution. Because the Teflon coating outside the wells is hydrophobic, the aqueous samples do not spill out. The format of a carrier slide can be designed to fit certain applications. For example, a single row of 8 wells on a slide can be used to analyze 8 samples. Furthermore, a 4×8 array of wells can be used to analyze 32 samples. Similarly, more wells (e.g., 96, 384, and 1536) can be arranged on a single slide to analyze more samples.

In certain embodiments of a mobile chip carrier, chips are bonded to a substrate such as glass, stainless steel, plastic materials, silicon, or ceramic materials. The whole carrier unit is movable and can be transported during processing to expose the chips to different reaction media, such as reaction chambers, washing chambers, and signal reading stages.

In other embodiments, the mobile chip carrier comprises a chamber or chambers in which the chips are secured. By housing the chips inside the mobile chip carrier, contamination during transport can be minimized. In certain embodiments, the chamber or chambers of the mobile chip carrier also serve as a processing environment. Reactive gases or liquid solutions for various purposes, such as performing a bioassay or cleaning the chips, may be admitted into the chamber and subsequently evacuated, if desired. Additionally, the mobile chip carrier may possess means for changing the thermodynamic properties of the chamber, such as the chamber pressure or temperature.

V. Assays

The biochips of the invention comprising bead arrays are useful for conducting various bioanalytical and chemical assays. Once assembled, the bead arrays on the biochips of the invention may be imaged to record assay signals and may be decoded to identify target analytes bound to the probes associated with individual beads within the array. The bead array provides a system which can be used to read the results of multistep bioanalytical or chemical assay sequences. In addition, multiple target analytes are capable of being detected simultaneously due to the presence of a plurality of probes directed to different target analytes comprising the arrays. Besides providing the ability to detect the presence or absence of specific target analytes, the bead arrays of the invention also find applicability in the determination of affinity constants for the target analytes which bind to the probes. Thus, the biochips have broad applicability to detect for example, biomolecules such TNF-alpha and Il-6. Other non-limiting applications include genotyping by polymorphism analysis; gene expression analysis; quantitative multiplexed profiling of cytokine expression, analysis of genes and gene products within the same fluid sample; affinity fingerprinting; and multiplexed analysis of reaction kinetics. Other assays and analytical determinations, such as those referred to in U.S. Pat. No. 6,327,410, which is incorporated herein by reference, may be adapted for use with the biochips of this invention.

EXAMPLES

The present invention will be better understood from the Examples which follow. However, one skilled in the art will readily appreciate that the specific methods and results discussed are merely illustrative of the invention described in the claims which follow thereafter.

Example 1

Wafer Fabrication and Design of Chips Comprising Bead Arrays

Figure 11:
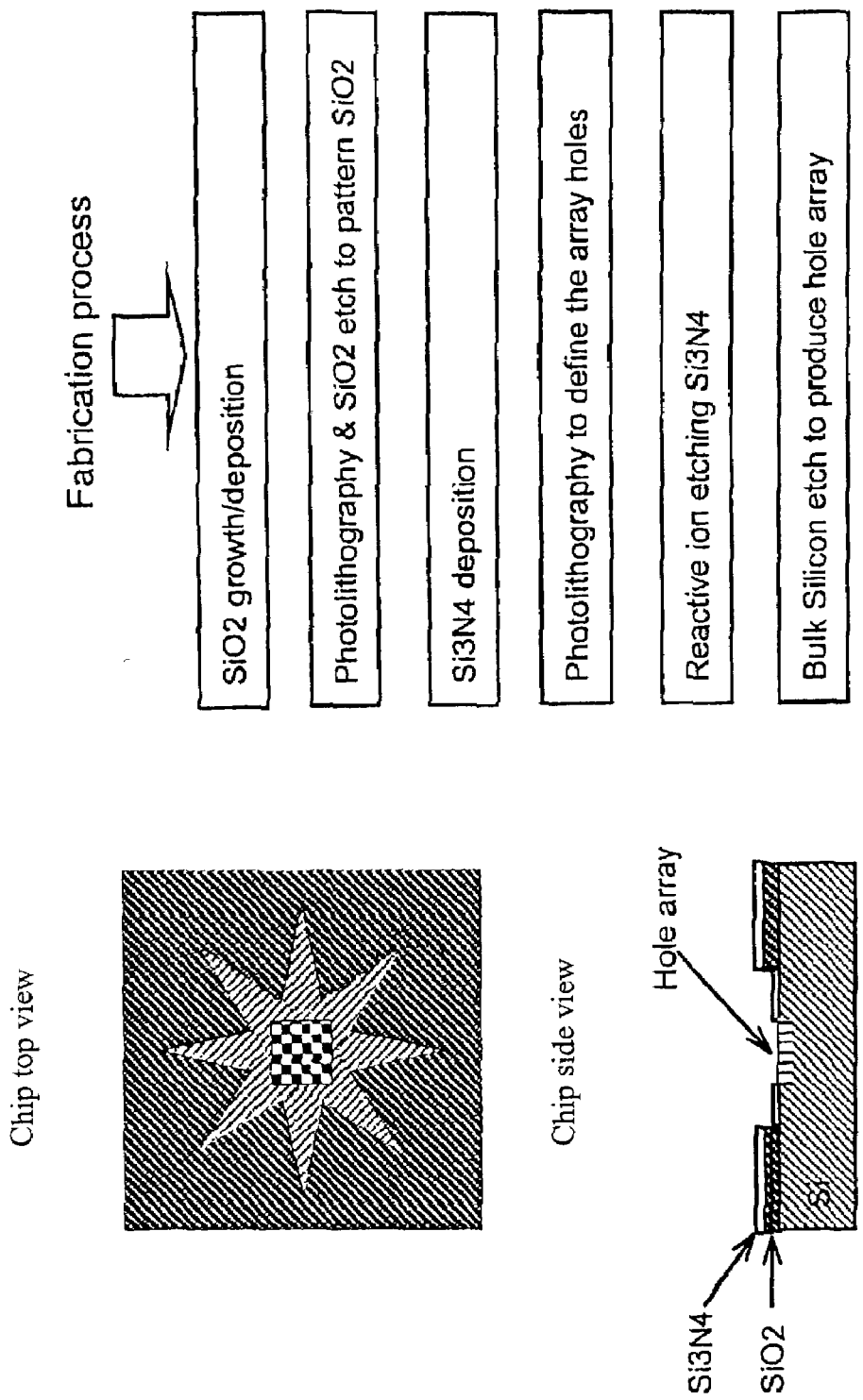
FIG. 11 illustrates the fabrication method for the chips comprising bead arrays of the invention.

The fabrication process of the chip comprising a bead array, as shown in FIG. 4, is described in FIG. 11. The substrate was a 100 mm diameter, 0.5 mm thick, silicon wafer with crystal orientation of (100), n-type phosphorus doped. A suitable resistivity range for these wafers is 1.5-4$\Omega$-cm. Wafers were usually fabricated in batches of up to 25. The first step comprises $SiO_2$ growth. The wafers were first cleaned by the RCA cleaning process, which comprises the steps of (1) soaking the wafers in a mixture of $NH_4OH$:$H_2O_2$ (30%):$H_2O$ in a volume ratio of 1:1:5 at 75° C. for 10 minutes; (2) rinsing with a cascade water batch cleaning using 18 M$\Omega$-cm water; (3) soaking the wafers in a mixture of HCl (36%):$H_2O_2$ (30%):$H_2O$ in a volume ratio of 1:1:5 at 75° C. for 10 minutes; and (4) rinsing with a cascade flow water batch cleaning until the water in the bath is at least 16 M$\Omega$-cm. The wafers were spun dry before being placed in a horizontal furnace for $SiO_2$ growth. The wafers were placed vertically on a quartz boat and introduced to an oxidation furnace at 1050° C. which had $O_2$+HCl(4%) at a pressure of 760 torr. The oxidation time was 34 minutes. A uniform 1000 Å $SiO_2$ layer was obtained by this method, as verified using ellipsometry (refractive index: n=1.46, thickness variation: <5%).

The wafers with $SiO_2$ were spin-coated with photoresist (Shipley 1813) at a spin rate of 4000 rpm (spin time 30 seconds), then baked on a hot plate at 115° C. for 60 seconds to remove the solvent. The wafer was then exposed to UV light (365-405 nm) in a contact lithography step which used Hybrid Technology Group's (HTG) system 3 HR contact/proximity mask aligner. Following UV exposure, the wafer was developed by AZ300 MIF developer for 60 seconds, rinsed in DI water and blown dry with a stream of compressed dry nitrogen. The wafers were then submerged in buffered oxide etchant (6:1 mixture of ammonium fluoride and 50% aqueous hydrogen fluoride) for 2 minutes to etch away the $SiO_2$ on the exposed area (the star in FIG. 11). The wafers were subsequently rinsed with DI water, then soaked in 1165 Microposit photoresist remover at 60° C. for 60 minutes to remove the photoresist. The wafers were then rinsed in DI water and blown dry with the jet of dry compressed nitrogen. This entire procedure results in wafers with a patterned oxide layer.

Following the oxide patterning step, the wafers were cleaned by the RCA process, and then placed in a horizontal furnace for silicon nitride ($Si_3N_4$) deposition. Two types of silicon nitride can be used: standard and low stress nitride. The conditions for deposition are as follows: LPCVD nitride (standard), pressure=200 mtorr, temp=800° C., $SiCl_2H_2$=30 sccm, $NH_3$=90 sccm; LPCVD nitride (low stress): pressure=150 mtorr, temp=850° C., $SiCl_2H_2$=47 sccm, $NH_3$=10 sccm. After 2 to 3 minutes of deposition, the $Si_3N_4$ film thickness is between 60-90 Å.

The next step is to fabricate the array structures. The wafers were spin-coated with photoresist OCG 12i at a spin rate of 4000 rpm (spin time 30 seconds) and then baked on a hot plate at 90° C. for 60 seconds to remove solvent. The wafers were exposed to UV light (365 nm) and repeat lithography was performed using a GCA-6300 10x i-line Stepper. After exposure, the wafer was baked on a hotplate at 115° C. for 90 seconds before being developed by AZ300 MIF developer for 60 seconds, rinsed in DI water, and blown dry with stream of compressed dry nitrogen. The wafers were baked in a 90° C. oven for 20 minutes. The wafers were then etched in a Plasma Therm 72 etcher to remove the silicon nitride in the exposed area (the hexagonal features in the arrays) using $CF_4$ gas reactive ion etching. Oxygen reactive ion etching was then used to remove residual polymeric material on the hexagonal features. The hexagonal recesses were fabricated by Deep Reactive Ion Etching (DRIE) using a Unaxis SLR 770 ICP Deep Silicon Etcher (licensed Bosch fluorine process). The process was adjusted so that it takes 2-3 minutes to etch 3.8 micron-deep recesses. The control of the depth is within 0.3 microns. After etching, the wafers were soaked in 1165 Microposit photoresist remover at 60° C. for 60 minutes to remove the photoresist. The wafers were rinsed in DI water and blown dry with a jet of dry compressed nitrogen. The wafers were then processed in a GaSonics, Aura 1000, Downstream Photoresist Stripper by oxygen plasma for 90 seconds to remove any residual polymer inside the hexagonal recesses generated during the DRIE process. The wafers were then spin-coated with a protective photoresist coating (Shipley 1813, spin rate of 4000 rpm, spin time 30 seconds), then baked on a hot plate at 115° C. for 60 seconds to remove solvent. The wafers were sent out to a commercial vendor for backside coating of 500 Å of gold with 100 Å of chromium as the adhesion layer. The backsides of the wafers were stripped of the native silicon oxide layer immediately prior to the coating process using argon ion sputtering.

The fabricated wafers were saw cut on the surface to define each chip (dimensions of each chip, 1.75×1.75 mm square). The depth of the cuts were ⅔ of the thickness of the wafers. After saw cutting, the wafers were cleaned by soaking them in 1165 Microposit photoresist remover at 60° C. for 60 minutes to remove the photoresist, then rinsing in DI water and blowing dry with a stream of compressed dry nitrogen. Usually the wafers were then soaked in NanoStrip (a mixture of concentrated sulfuric acid and hydrogen peroxide) at 60° C. for 2 hours, then rinsed in DI water and blown dry with a stream of compressed dry nitrogen. After these procedures, the wafers are ready for the bead assembly step.

After bead assembly, the extra beads that are not secured in recesses may be removed. One method for removing unsecured beads is to wipe the chip or wafer surface with moistened cotton applicators. Another method is to wash away the unsecured beads using water jets nearly parallel to the chip or wafer surface. Yet another method comprises growing a gel on the surface and subsequently peeling off the gel.

Example 2

Functionalization of Beads and Formation of a Bead Array

Color encoded, tosyl-functionalized beads of 3.2 µm diameter were used as solid phase carriers. Several sets of distinguishable color codes were generated by staining particles using standard methods (Bangs. L. B., "Uniform Latex Particles", Seragen Diagnostics Inc., p.40). Stained beads were functionalized with Neutravidin (Pierce, Rockford, Ill.), a biotin binding protein, to mediate immobilization of biotinylated probes or primers. In a typical small-scale coupling reaction, 200 µl of suspension containing 1% beads were washed three times with 500 µl of 100 mM phosphate buffer/pH 7.4 (buffer A) and resuspended in 500 µl of that buffer. After applying 20 µl of 5 mg/ml neutravidin to the bead suspension, the reaction was allowed to proceed overnight at 37° C. Coupled beads (i.e., beads with bio-functional molecules attached thereto) were then washed once with 500 µl of PBS/pH 7.4 with 10 mg/ml BSA (buffer B), resuspended in 500 µl of that buffer and reacted for 1 hour at 37° C. to block unreacted sites on bead surface. After blocking, beads were washed three times with buffer B and stored in 200 µl of that buffer.

Probes (for the detection of target molecules) and primers (which can be used as templates to extend the hybridized DNA target for subsequent catalytic reactions to identify the reacted probes) that were to be coupled to the beads were biotinylated at the 5' end; a 15-carbon triethylene glycol linker was inserted between biotin and the oligonucleotide to minimize disruptive effects of the surface immobilization on the subsequent reactions. For each primer, a binding reaction was performed using 50 µl of bead suspension. Beads were washed once with 500 µl of 20 mM Tris/ pH 7.4, 0.5M NaCl (buffer C) and resuspended in 300 µl of that buffer. A primer solution (2.5 µl of a 100 µM solution) was added to the bead suspension and allowed to react for 30 minutes at room temperature. Beads were then washed three times with 20 mM Tris/pH7.4, 150 mM NaCl, 0.01% triton and stored in 20 mM Tris/pH 7.4, 150 MM NaCl.

An exemplary bead array was assembled as follows. The bead suspension obtained through the procedures described above was washed with de-ionized water (All water used was highly purified and sterilized with a resistivity of 18 MΩ-cm or higher) five times before being suspended in 0.01 mM of TRIS Base+0.01% Triton x–100 water solution. The bead content of the suspension was 0.5%. Two microliters of the bead suspension was added to the surface of a 4.5 mm square chip comprising a bead array by micro-pipet. The chip was then subjected to the process of LEAPS. The counter electrode was a piece of glass coated by a layer of indium tin oxide (ITO). The gap between the surface of the chip and the ITO-coated glass was 100 microns. AC power was applied in the sequence listed in Table 1.

TABLE 1

AC supply sequence.
The voltage is half of the peak-to-peak amplitude.

| Step | Time (minutes) | Frequency (Hz) | Voltage (± volts) | Function |
|---|---|---|---|---|
| 1 | 2 | 2000 | 3 | AC on |
| 2 | 2 | 1000 | 3 | AC on |
| 3 | 2 | 500 | 3 | AC on |
| 4 | 2 | 2000 | 3 | AC on |
| 5 | 2 | 500 | 3 | AC on |
| 6 | 2 | 2000 | 3 | AC on |
| 7 | 2 | 200 | 3 | AC on |
| 8 | 2 | 2000 | 3 | AC on |
| 9 | 2 | 200 | 3 | AC on |
| 10 | 0 | 200 | 0 | AC stop |

After the sequence was completed, the beads within the area spanned by the star shaped pattern were concentrated in the array area. The flow pattern induced by the presence of the star-shaped pattern helps to concentrate the beads. After waiting 15 minutes for the beads to settle, the device was slowly soaked in pure water. The ITO glass coating was slowly lifted, and the water was slowly drained so that the chip surface emerged. At this point, the surface could be dried by either leaving the chip at room temperature for an extended period or by baking the chip in an oven at 55° C. for 5 minutes. The dried chip was soaked in pure water for 15 minutes, and then the chip surface was gently wiped with a wet cotton swab several times to remove the beads that were not in the array. The chip was subsequently rinsed with pure water three times before being dried by blowing compressed nitrogen on its surfaces. Finally, the chip was inspected by fluorescence light microscopy to ensure that no extra beads were outside the array.

Example 3

Forming a Bead Array

A bead slurry was directly dispensed onto the array area on a chip. A wet cotton applicator (K1) was used to gently stir the bead slurry on the array surface. The motion of K1 can be circular, linear or some other meaningful mode, and is usually parallel to the chip surface. After stirring the slurry several times, the beads were moved into the array. Then, the chip surface was cleaned by using K1 to wipe away extra beads that were not in the array. This process can be scaled up from single chips to wafer-scale multi-chip assembly, and can be automated.

An example of a processing procedure for forming bead arrays is as follows. Two microliters of 1% microparticles (approximately 3.2 micrometers in diameter) in 100 microliters of phosphate-buffered saline (also known as PBS: 150 mM, NaCl; 100 mM, NaP, pH 7.2) were used for assembling eight microparticle arrays on silicon chips (2.5×2.5 mm) with 4,000 microwells on each chip. The following procedures were used:

(1) Microparticles from PBS were collected in an 1.5 ml centrifuge tube by centrifugation (14,000 g, 1 minute). Other collection means may be used.
(2) The supernatant was discarded by aspiration using a transfer pipet.
(3) The particles were re-suspended in 5 microliters of 5% glycerol in 10 mM Tris pH 7.5.
(4) The particles were collected from the glycerol solution by centrifugation. Other collection means may be used.
(5) The glycerol solution was aspirated from the particle pellets.
(6) The pellets were re-suspended in 1 microliter of the 5% glycerol, 10 mM Tris, pH 7.5.
(7) Eight silicon chips were placed on a double-sided tap attached on a microscope slide.
(8) A 0.1 microliter volume of the particle suspension was pipetted onto each of the chips in the area with 4,000 microwells.
(9) A cotton applicator was washed with water from a wash bottle.
(10) The wet cotton applicator was blown dry for 30 seconds by using pressured air. The airflow removes excess water from the cotton of the applicator. In addition, the air also blows out some fibers from the surface, which makes the cotton ball more fluffy.
(11) Due to evaporation of the bead suspension in the air and hygroscopic nature of glycerol in the solution, by the time steps 9 and 10 were completed (about1-2 minutes), the water content in the suspension from step 8 reached equilibrium. Because of increased viscosity, the droplet became more of a slurry. To assemble microparticle arrays, the bead slurry was gently stirred with the tip of the wet cotton applicator in a circular motion several times. The loose fibers of the cotton ball ferried the beads into the microwells on the surface (FIG. 3).

(12) The particle occupancy of the microwells was examined by using a fluorescent microscope. If the occupancy is not satisfactory, step 11 can be repeated.

(13) Excess particles were gently wiped away from the chip by using the cotton applicator. To avoid excess water on the surface, the cotton applicator was not pressed against the chip.

(14) The chip was dried by blowing on the surface of the chip with compressed nitrogen.

(15) The assembled microparticle prepared by this method can be used for assays or stored in solution at 4° C. for later use.

In this example, the microparticles are suspended in a small amount of 5% glycerol, 10 mM Tris pH 7.5 solution for direct deposition of microparticle arrays on the silicon chip. However, while the particles may be suspended in other solutions, if LEAPS is used to assemble the beads, high solution viscosity or ionic concentration may interfere with LEAPS, (e.g., with the assembly of particles on designated areas of a substrate such as a patterned or illuminated electrode). Accordingly, it is recommended that the ionic concentration of the suspension be about 1.0 mM or lower, preferably between about 0.1 mM to 1.0 mM. In addition, it is recommended that the viscosity of the suspension be about 100 cp or less.

In addition, certain salts, such as sodium phosphate and sodium chloride, may form crystals at the elevated concentrations that occur during step 11. Such crystals may interfere with bio-molecules on bead surfaces. Accordingly, they are not recommended for use in bead suspensions.

Example 4

Direct Deposition

The direct deposition method disclosed in the present application is a simple approach for assembling microparticle arrays on a solid surface efficiently. For example, a 0.25 microliter volume of 1% microparticle solution (10 mg/ml, which corresponds to 168,000 beads), is enough for assembling arrays on a silicon chip containing 4,000 microwells with higher than 95% occupancy. In other words, it takes about 2% of the beads in suspension to fill in the microwells at the surface. In addition, the assembly process is carried out in water solution with neutral pH, at room temperature. These mild conditions assure that the reactivity of molecules such as DNA, RNA, peptides, and proteins, when immobilized on the particles, remains unchanged in the assembly. In this way, the microparticle arrays assembled using this method are compatible with various biochemical assays. Furthermore, the assembly process can be scaled up from single chip assembly to wafer-scale assembly, and can be automated to produce large numbers of microparticle arrays.

The direct deposition method is further illustrated by the following example. A volume of 2 microliters of a 1% microparticle solution (microparticles approximately 3.5 micrometers in diameter) were added to 100 microliters of phosphate-buffered saline (also known as PBS: 150 mM, NaCl; 100 mM, NaP, pH 7.2) to form eight microparticle arrays on silicon chips (2.5×2.5 mm) with 4,000 microwells on each chip. The procedure was as follows:

(1) Microparticles were collected from the PBS in an eppentof tube by centrifugation (14,000 g, 1 minute). Other collection means may be used.

(2) The supernatant was discarded by aspiration using a transfer pipet (3) The particles were re-suspended in 5 microliters of 5% glycerol in 10 mM Tris pH 7.5.

(4) The particles were collected from the glycerol solution by centrifugation. Other collection means can be used.

(5) The glycerol solution was aspirated from the particle pellets.

(6) The pellets were re-suspended in 1 microliter of the 5% glycerol, 10 mM Tris, pH 7.5 solution.

(7) Eight silicon chips were placed on a double-sided tap attached to a microscope slide.

(8) A volume of 0.1 microliter of the particle suspension was pipetted onto each of the chips in the area with 4,000 microwells.

(9) The cotton applicator was washed with water from a wash bottle.

(10) The wet cotton applicator was blown dry for 30 seconds by using pressurized air. The airflow removes excess water from the cotton applicator. In addition, the air also blows out some fibers from the surface, which makes the cotton ball more fluffy.

(11) Due to evaporation of the bead suspension in the air and the hygroscopic nature of the glycerol in the solution, by the time steps 9 and 10 were finished (1-2 minutes), the water content in the suspension from step 8 reached equilibrium. Because of increased viscosity, the droplet becomes a slurry. To assembly microparticle arrays, the bead slurry was gently stirred with the tip of the moistened cotton applicator in a circular motion several times. The loose fibers of the cotton ball will ferry the beads into the microwells on the surface.

(12) The particle occupancy of the microwells was examined by using a fluorescent microscope. Step 11 was repeated in cases where the occupancy was not satisfactory.

(13) Excess particles were gently wiped away from the chip by using the cotton applicator. To avoid excess water on the surface, the cotton applicator was not pressed against the chip.

(14) After step 13, the assembled microparticle arrays were ready for assays, or for storage in solution at 4° C. for later use.

For assembling arrays using direct deposition, it is useful to use microparticles suspended in small amount of 5% glycerol, 10 mM Tris pH 7.5 solution. The use of concentrated glycerol, (i.e. higher than 5%), may increase the viscosity of the bead slurry, and the specific gravity of the solution in the droplet on the chip (step 11). In turn, this may comprise the assembly efficiency. Although the solution used for the direct deposition method is not limited to 10 mM Tri, pH 7.5, it should be noted that certain salts, such as sodium phosphate and sodium chloride, tend to form crystals in elevated concentrations, such as in step 11. The salt crystals not only serve to reduce the occupancy of microparticles in the wells, but also may damage molecules on the surface during assembly.

It is also recommended to store the assembled chips or wafers comprising chips in a humid chamber for a short period of time (e.g. 30 min) to allow the beads to settle down in the recesses by gravity before being used in an assay. Centrifugation of assembled arrays bound to a glass slide may facilitate the settling process. Recommended settings for the centrifugation are as follows:

| | |
|---|---|
| Centrifuge: | Sorvall centrifuge model RT6000B |
| Rotor: | Sorvall swing bucket model H1000B |
| Speed: | 2000 RPM |
| Time: | 5 min |
| Operation note: | Set the centrifuge at refrigerated mode at 10° C. Set the brake at off mode Slow ramp up the speed from 0 to 2000 in the first 2 min followed by centrifugation at 2000 RPM an additional 5 min. Equivalent equipment and settings may be used for this process. |

Viscous immersion media are useful for mounting the chips on the slide for microscope examination. One example is to use mounting media containing 2.25 M tetrathylammonium chloride, 37.5 mM Tris, pH 8.0, 25% glycerol.

Example 5

Parallel Assembly of Biochip Arrays

The present invention provides methods for parallel assembly of biochip arrays. In this embodiment, the biochip arrays are formed from chips that originate from different wafers. A non-limiting example is illustrated by FIG. 9, which shows four different wafers giving rise to four types of chips: A, B, C, and D. Rows or columns of chips may be combined in any geometry to form an intermediate chip matrix. In preferred embodiments, the chips have a regular geometric shape, (for example, a square or rectangle), and the corresponding intermediate chip matrix also has a regular geometric shape. Rows or columns are then extracted from the intermediate chip matrix, such that the rows or columns comprise different types of chips. Depending on the application, the mixed rows or columns may contain more than one copy of a certain type of biochip. The mixed rows and/or columns formed in these embodiments can be incorporated into biochip arrays for bioassays. In preferred embodiments, semiconductor chip-handling equipment is used to assemble the intermediate chip matrix and to extract the mixed rows or columns. By using long rows or columns of chips to form the intermediate chip array, it is possible to generate many mixed rows or columns simultaneously. In this way, it is possible to mass-produce the mixed rows or columns.

Example 6

Biochip Protection by Saccharide Coating

Functionalized beads were assembled on a chip using standard procedures. Following assembly, the chip surface was cleaned, and 2-4 µl of 1% solution of trehalose (alpha-D-glucopyranosyl alpha-D-glucopyranoside, a naturally-occurring, glass-forming disaccharide) in DI water was dispensed on the chip (surface dimension: 1.75×1.75 mm) and allowed to dry under ambient conditions. On drying, a glassy film formed on the substrate and encapsulated the assembled beads. Although the film is stable even under high humidity conditions, exposure to liquid water dissolves the film instantly.

To evaluate the effect of the film formation on the activity of the functionalized particles, neutravidin-functionalized particles were assembled on biochips. Some biochips were passivated with trehalose solution as described above and subjected to normal ambient conditions, while other biochips were not coated with trehalose solution but instead stored at 4° C. for 2 weeks. It was found that the bioactivity of the bio-coated chips was similar to that of the non-coated biochips kept at 4° C.

Example 7

Hydrogels as Multifunctional Agents in Wafer Cleaning, Storage and Particle Recovery Agarose hydrogel can be employed as a peeling agent to remove the particles from a chip in a manner that permits them to be retrieved later. The hydrogel also can be used as a storage material to prevent wafer and particles from dehydration and dust.

Functionalized particles were assembled on a 6inch wafer comprised of chips. To clean the particles left on the surface, a 1% agarose solution at 55° C. (melting point 95° C., gelation temperature 50° C.) was poured onto the wafer, and kept under ambient conditions or at 4° C. until the gelation occurs. Gels with different thickness, from micrometers to millimeters, can be produced by using spacers of different thickness. The spacers provide a barrier at the edge of the wafer to prevent the agarose solution from running off the edge. The beads located on the surface of the wafer, rather than inside the recesses, will be embedded in the gel. After the solution is completely solidified, the gel film, as well as embedded beads, can be easily peeled off. A compressed nitrogen stream is then applied immediately to blow dry the small amount of water residue on the surface. In this way, the wafer surface remains clean.

To assess the effect of the peeling procedure on the occupancy, as well as the effect of the agarose gel film on the activity of the functionalized particles, the particles were assembled on the chips and the chips were then subjected to decoding analysis and extension assays. FIG. 12 showed that the peeling procedures did not decrease the occupancy (i.e. no particles were pulled out of recesses). It is believe that the viscosity of the gel solution plays a role in maintaining the particles inside of holes. With higher gel solution viscosities, tendency of solution to go into the recess before gelation decreases, so there is a lower probability that the occupancy is affected. An SSP on-chip assay indicated that the signal and CV were comparable (FIG. 13ab), indicating that the gel does not affect the assay sensitivity.

Agarose gel is a thermo-reversible physically crosslinked hydrogel. For the purpose of particle recovery, agarose with ultra low melting point (m.p. <50° C., gelation temperature, 8-17° C.) should be used. Subsequently, the agarose gel can be re-melted at 50-55° C., and the embedded particles can be retrieved. The biological activities of biomolecules on the particles are retained under these conditions.

Such hydrophilic hydrogels not only can be used as a peeling agent, but also as a storage agent to prevent particles/wafers from dehydration, dust and physical damage during the storage and shipping.

Example 8

Polymer Coating

A small batch of cleaned individual chips [about 5 to 20 in number] were placed in a small Teflon container (volume~5ml) filled with 1 ml of a 1% (1 mg/ml) solution of polyallylamine hydrochloride (Mw~15,000) or a 0.1% polylysine solution (Sigma Aldrich). The chips were incubated for 1-2 hr with gentle shaking at room temperature. Afterwards, they were removed from the polymer solution and dried for ~1 hr in the temperature range of 50-70° C. This treatment usually leaves behind a thick and uneven coating film of the polymer on the surface of the chip. These modified chips were used for assembling beads using standard protocols. The surface cleaning step at the end of the assembly process removed most of the excess polymer along with the excess beads. The presence of the polymer coating improved the adhesion of the beads to the chip surface and the retention of the beads in the recesses were considerably improved after such a treatment.

Example 9

Biochip Packaging to Form Multi-chip Carriers for Biological Assays and Addition to Bead Arrays and Methods of Preparation Thereof The type of packaging chosen for a particular biochip depends on the application. Usually, one or more biochips are affixed on a chip carrier for convenience. The carriers can be as simple as glass slides, or they can be complicated cartridges with fluidic handling, temperature control, signal recording, and other functions. The biochips can be bonded to the carrier permanently by glue or reversibly bonded by various means such as magnetic or mechanical forces.

Example 9A

A Multi-Chip Carrier made from a Glass Slide

To prepare the slide as a carrier, a Teflon coating is applied in such a manner as to leave circular openings or wells (i.e., areas of glass without any Teflon covering). Each well is a circle with 6.5 mm in diameter. One or more chips can be bonded to the glass surface within a well. A typical glass slide is 25×75 mm and 1 mm thick, with a 2×5 array of wells. With typical chip sizes of 1.75×1.75 mm, up to four chips can be bonded to the glass surface in each well. Each chip in the same well can have distinct bead groups that were assembled prior to bonding to the carrier. For example, if each chip has an array containing 39 types of bead groups, a well with 4 distinct chips would have a total of 4×39=156 types of beads. On the other hand, for larger chips (e.g., a 4.5×4.5 mm square) an entire well is occupied by a single chip. For the well dimensions described herein, each well can hold up to 40 µl of liquid (usually an aqueous solution). Typically, a 20 µl volume of sample solution is added to each well for biological reactions, such that each chip is totally covered by the sample solution. Because the Teflon coating outside the wells is hydrophobic, the aqueous samples do not spill out. The format of a carrier slide can be designed to fit certain applications. For example, a single row of 8 wells on a slide can be used to analyze 8 samples. Furthermore, a 4×8 array of wells can be used to analyze 32 samples. Similarly, more wells (e.g., 96, 384, and 1536) can be arranged on a single slide to analyze more samples.

Example 9B

Mobile Chip Carrier

In certain embodiments of a mobile chip carrier, chips are bonded to a substrate such as glass, stainless steel, plastic materials, semiconductors, or ceramic materials. The whole carrier unit is movable and can be transported during processing to expose the chips to different reaction media, such as reaction chambers, washing chambers, and signal reading stages. (See FIG. 14 for an embodiment).

In other embodiments, the mobile chip carrier comprises a chamber or chambers in which the chips are bonded. By housing the chips inside the mobile chip carrier, contamination during transport can be minimized. In certain embodiments, the chamber(s) of the mobile chip carrier also serve as a processing environment. Reactive gases or liquid solutions for various purposes, such as performing a bioassay or cleaning the chips, may be admitted into the mobile chip carrier and subsequently evacuated, if desired. Additionally, the mobile chip carrier may possess means for changing the thermodynamic properties of the chamber, such as the chamber pressure or temperature.

Example 10

Assembly of Encoded Chip Arrays by Random Tiling

A multiplicity of chips can be produced by the assembly of random encoded arrays of probes that are displayed on beads. Each chip may include one or more random encoded bead arrays and may be cut from a uniquely identified wafer. As illustrated in FIG. 15(a, b, c and d), a random encoded array of chips may be produced in a tiling process. This process may be facilitated by a choosing an appropriate chip shape in order to facilitate alignment and to maximize interlocking placement to decrease the array-to-array distance.

We claim:

1. A method for producing biochips comprising patterning a substrate, having at least one surface, to form a plurality of biochip regions; by inscribing the substrate between the chip regions; assembling bead arrays comprising many differently optically encoded beads having biomolecules attached thereto said biomolecues being identified by said optical encoding, said assembly occurring on a surface of the substrate within several of the biochip regions but without encoding the location of each biochip region within the substrate; and singulating the substrate along at least some of the inscriptions to form a plurality of individual biochips with assembled bead arrays thereon.

2. The method according to claim 1, wherein the substrate is a semiconductor wafer.

3. The method of claim 1 wherein the scribing is by deep reactive ion etching.

4. The method of claim 1 wherein the beads are color-encoded.

5. The method of claim 4 wherein the color-encoding is with fluorescent dyes.

6. The method of claim 1 wherein the biomolecules are nucleic acids, including DNA and RNA or proteins.

7. The method of claim 1 wherein the beads are held to the biochip surface by van der Waals forces.

8. The method of claim 1 further including adding a coating, wherein the coating is a non-reducing sugar.

9. The method of claim 1 further including placing biochips on a substrate.

10. The method of claim 1 further including tagging the biochips originating from a first wafer with a binary code, and combining at least one tagged biochip from the first wafer with at least one biochip from a second wafer, tagged with a binary code and placing the tagged biochips on the substrate.

11. The method of claim 1 wherein the biochips are tagged with a binary code.

12. The method of claim 11 wherein tags indicate the substrate of origin of the biochips.

* * * * *

UNITED STATES PATENT AND TRADEMARK OFFICE
CERTIFICATE OF CORRECTION

| | | |
|---|---|---|
| PATENT NO. | : 7,335,153 B2 | Page 1 of 1 |
| APPLICATION NO. | : 10/192352 | |
| DATED | : February 26, 2008 | |
| INVENTOR(S) | : Michael Seul et al. | |

It is certified that error appears in the above-identified patent and that said Letters Patent is hereby corrected as shown below:

Claim 10, column 30, line 54, change "claim 1" to --claim 9--.

Signed and Sealed this

Twenty-seventh Day of January, 2009

JOHN DOLL
*Acting Director of the United States Patent and Trademark Office*